United States Patent
Yamamichi et al.

(10) Patent No.: US 8,638,442 B2
(45) Date of Patent: *Jan. 28, 2014

(54) SUBSTRATE OF TARGET SUBSTANCE DETECTION ELEMENT TO BE USED IN APPARATUS FOR DETECTING TARGET SUBSTANCE BY UTILIZING SURFACE PLASMON RESONANCE AND DETECTION ELEMENT AND DETECTION APPARATUS USING SAME

(75) Inventors: Junta Yamamichi, Yokohama (JP); Tetsunori Ojima, Kawasaki (JP); Hidenori Shiotsuka, Kawasaki (JP)

(73) Assignee: Canon Kabushiki Kaisha, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 13/177,345

(22) Filed: Jul. 6, 2011

(65) Prior Publication Data
US 2011/0263458 A1    Oct. 27, 2011

Related U.S. Application Data

(62) Division of application No. 10/582,805, filed as application No. PCT/JP2006/309222 on Apr. 27, 2006, now Pat. No. 8,004,685.

(30) Foreign Application Priority Data

Apr. 28, 2005 (JP) ................. 2005-132929
Dec. 22, 2005 (JP) ................. 2005-370756

(51) Int. Cl.
*G01N 21/55* (2006.01)

(52) U.S. Cl.
USPC ....................................... 356/445

(58) Field of Classification Search
USPC ........................ 356/445–448; 436/525; 435/6
See application file for complete search history.

(56) References Cited

U.S. PATENT DOCUMENTS

| 6,570,657 B1 | 5/2003 | Hoppe et al. |
| 6,614,742 B2 | 9/2003 | Ueyanagi |
| 6,949,732 B2 | 9/2005 | Kiguchi et al. |
| 6,977,767 B2 | 12/2005 | Sarychev et al. |
| 7,057,151 B2 | 6/2006 | Lezec et al. |

(Continued)

FOREIGN PATENT DOCUMENTS

| JP | 2003-28774 A | 1/2003 |
| JP | 2003-270132 A | 9/2003 |

(Continued)

OTHER PUBLICATIONS

Chang, et el., "The Shape Transition of Gold Nanorods", Langmuir, vol. 1999, No. 15, Dec. 1998, pp. 701-709.

(Continued)

*Primary Examiner* — Hoa Pham
(74) *Attorney, Agent, or Firm* — Fitzpatrick, Cella, Harper & Scinto

(57) ABSTRACT

A substrate of a target substance detection element to be used for a detection apparatus for detecting a target substance, utilizing surface plasmon resonance, comprises a base and a metal structure arranged on the surface of the base in a localized manner or a metal film having an aperture and arranged on the surface of the base, the metal structure or the aperture, whichever appropriate, having at least either of a loop section and a crossing section.

14 Claims, 18 Drawing Sheets

(56) References Cited

U.S. PATENT DOCUMENTS

| | | |
|---|---|---|
| 7,136,166 B2 | 11/2006 | Yamada et al. |
| 7,399,445 B2 | 7/2008 | Kuroda et al. |
| 7,544,922 B2 | 6/2009 | Ueyanagi et al. |
| 7,733,491 B2 | 6/2010 | Kuroda et al. |
| 7,915,053 B2 | 3/2011 | Yamamichi et al. |
| 8,004,685 B2 * | 8/2011 | Yamamichi et al. ......... 356/445 |
| 2003/0224441 A1 * | 12/2003 | Nakamura et al. ............. 435/6 |
| 2005/0053974 A1 | 3/2005 | Lakowicz et al. |
| 2006/0072114 A1 | 4/2006 | Sigalas et al. |
| 2006/0108219 A1 * | 5/2006 | Kuroda et al. ............ 204/403.1 |

FOREIGN PATENT DOCUMENTS

| | | |
|---|---|---|
| JP | 3452837 B2 | 10/2003 |
| JP | 2004-335569 A | 11/2004 |
| JP | 2005-312446 A | 11/2005 |
| WO | 2004/113880 A2 | 12/2004 |
| WO | 2005/095461 A2 | 10/2005 |

OTHER PUBLICATIONS

Aizpurua, et al., "Optical Properties of Gold Nanorings", Physical Review Letters, vol. 90, No. 5, Feb. 7, 2003, pp. 057401-1-057401-4.

Lamprecht, et al., "SHG studies of plasmon dephasing in nanoparticles", Applied Physics B, Lasers and Optics, vol. 68, 1999, pp. 419-423.

UENO, vol. 363, Mar. 2005, pp. 153-154.

Official Action dated Dec. 20, 2010 in Canadian Application No. 2,606,182.

* cited by examiner

100

102

103

103

SUBSTRATE OF TARGET SUBSTANCE DETECTION ELEMENT TO BE USED IN APPARATUS FOR DETECTING TARGET SUBSTANCE BY UTILIZING SURFACE PLASMON RESONANCE AND DETECTION ELEMENT AND DETECTION APPARATUS USING SAME

This application is a divisional of Application No. 10/582,805, which was the National Stage of International Application No. PCT/JP2006/309222, filed Apr. 27, 2006. The contents of each of the foregoing applications is incorporated herein by reference.

TECHNICAL FIELD

This invention relates to a substrate of a target substance detection element to be used in an apparatus for detecting the presence or absence of a target substance in a specimen by utilizing surface plasmon resonance and also to a detection element and a detection apparatus realized by using such a substrate.

BACKGROUND ART

Detection methods for detecting substances existing near metal micro-particles by fixing metal micro-particles to the surface of a substrate and utilizing localized surface plasmon resonance induced there are known. More specifically, such methods utilize the fact that a characteristic resonance spectrum appears due to localized surface plasmon resonance when light is applied to metal micro-particles of gold or silver and the resonance wavelength depends on the permittivity of the medium existing near the metal micro-particles. For example, when the permittivity of the medium is raised, the absorbance of the resonance peak increases and the position of the resonance peak is shifted toward the long wavelength region. Sensors utilizing this phenomenon are also known. For example, Japanese Patent No. 3452837 discloses a sensor formed by arranging a plurality of metal micro-particles on a substrate so as to make them separated from each other. It is a surface plasmon resonance sensor for detecting the refractive index of the medium existing near the metal micro-particles by measuring the absorbance of light being transmitted through the sensor unit. More specifically, the sensor unit is formed by arranging gold colloids having a diameter of 20 nanometers. The sensor is advantageous relative to ordinary surface plasmon resonance sensors that comprise a unit, which includes a prism and a metal film formed on one of the surfaces of the prism to be brought into contact with a specimen and is adapted to be irradiated with light with various incident angles so as to observe the total reflection angle, in terms of that this invention requires neither a prism nor a special optical system and hence it can be a very compact sensor.

Apart from the above identified sensor, U.S. Patent Application Laid-open No. 2003-0132392 (Japanese Patent Application Laid-open No. 2003-270132) discloses a sensor adapted to induce surface plasmon resonance at a metal thin film having a plurality of apertures arranged periodically, wherein both the apertures and the gaps separating the apertures are smaller than the wavelength of light. According to the above cited patent document, as a result of periodically arranging aperture positions in a well-controlled manner, it can provide a high sensitivity sensor with a narrower resonance spectrum width and a higher resonance peak than micro-particle type sensors not having such a position control feature.

J. Phys. Chem. B 2004, 108, 109-116 describes a study on the sensitivity of the sensors realized by using metal nano-dots arranged on a substrate to induce localized surface plasmon and having a triangular profile and those having a spherical profile. The paper says that triangular metal nano-dots provide a sensitivity level higher than spherical ones.

While the surface plasmon resonance sensors disclosed in the above listed prior art documents are useful, they do not necessarily provide a satisfactory detection sensitivity level in affinity assays such as immuno assays utilizing the specificity of antigen-antibody reactions.

DISCLOSURE OF THE INVENTION

The present invention provides a substrate of a target substance detection element showing an improved detection sensitivity if compared with conventional surface plasmon resonance sensors.

In the first aspect of the present invention, there is provided a substrate of a target substance detection element to be used for a detection apparatus for detecting a target substance, utilizing surface plasmon resonance, comprising: a base and a metal structure arranged on the surface of the base in a localized manner, said metal structure having at least either of a loop section and a crossing section.

Further, in the second aspect of the present invention, there is provided a substrate of a target substance detection element to be used for a detection apparatus for detecting a target substance, utilizing plasomon resonance, comprising: a base and a metal film arranged on the surface of the base and having an aperture, said aperture having at least either of a loop section and a crossing section.

The present invention also provides a target substance detection element, a target substance detection apparatus, a target substance detection method and a target substance detection kit.

A target substance detection element according to the invention is an element for detecting a target substance, having a target substance capturing body arranged on a metal structure constituting the substrate according to the present invention.

A target substance detection apparatus according to the present invention is an apparatus for detecting a target substance in a specimen, comprising a holding means for holding a target substance detection element as defined above, a means for bringing the element into contact with the specimen and a detecting means for detecting the target substance captured by the element.

A target substance detection method according to the present invention is a method of detecting a target substance in a specimen, comprising a step of bringing a target substance detection element as defined above into contact with the specimen and a step of detecting the target substance captured by the element when the specimen contains the target substance.

A target substance detection kit according to the present invention is a kit for detecting the presence or absence of a target substance in a specimen or the quantity of the target substance, comprising a target substance detection element as defined above and an agent required to capture the target substance by means of the element.

According to the present invention, the metal structure for inducing surface plasmon resonance or the aperture of the metal film having the aperture is made to have at least either of a loop section and a crossing section. With this arrangement, it is possible to improve the detection sensitivity for detecting the substance to be detected.

In the mode of carrying out the present invention where the metal structure for inducing localized surface plasmon resonance has at least either of a loop section and a crossing section, the length of contour or the number of corners of the metal structure is increased because it has a loop section or a crossing section. As a result, the surface plasmon resonance is intensified to make it possible to improve the detection sensitivity for detecting a target substance.

In the mode of carrying out the present invention where the metal film has an aperture, on the other hand, the length of contour or the number of corners of the aperture is increased because it has a loop section or a crossing section. As a result, the surface plasmon resonance is intensified to make it possible to improve the detection sensitivity for detecting a target substance.

BEST MODE FOR CARRYING OUT THE INVENTION

Now, the present invention will be described in greater detail.
I. Element for Detecting a Target Substance
(First Embodiment)

The element (detection element) for detecting a target substance of this embodiment comprises at least a base, a number of metal structures for generating localized surface plasmon resonance arranged on the surface of the base and capturing bodies for capturing a target substance arranged on the metal structures. An element comprising a base and metal structures on which capturing bodies for capturing a target substance are not arranged can be provided as substrate for preparing a target substance detection element.

This element is made to show improved detection sensitivity for detecting a target substance by optimizing the arrangement of the metal structures and selecting a specific plane profile (metal pattern) for the metal structures. The term "plane profile" of metal structure as used herein refers to the profile thereof on a plane running in parallel with the substrate surface (base surface) and hence the profile in the plan view of the substrate surface as viewed from above.

According to the present invention, the plane profile of a metal structure has at least either of a loop section and a crossing section. FIGS. 1A through 1E and 2A through 2F illustrate schematic plan views of metal structures having various different profiles that can be used for the embodiment of the invention. FIGS. 1A through 1E show metal structures principally comprising a polygonal or circular loop section (going around structure), whereas FIGS. 2A through 2F show metal structures principally comprising a crossing section.

Figure 1A:
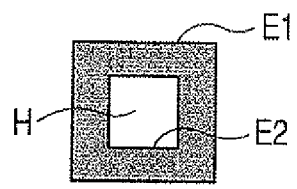
FIGS. 1A, 1B, 1C, 1D and 1E are schematic plan views of metal structures having various different plane profiles that can be used for embodiments of the present invention.
Figure 1B:
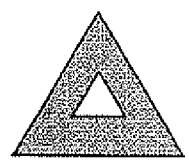
Figure 1C:
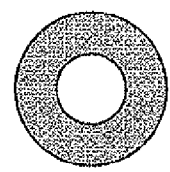
Figure 1D:
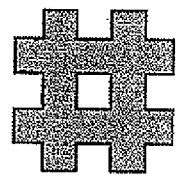
Figure 1E:
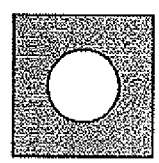

Plane profiles of metal structures comprising a loop section that can be used for the purpose of the present invention include ring-shaped ones having just a loop section as illustrated in FIGS. 1A through 1O and ones having a loop section as part thereof as illustrated in FIG. 1O. A ring-shaped profile having an inner contour and an outer contour that are different from each other as shown in FIG. 1E may also be used for the purpose of the present invention. A single metal structure may be made to have two or more than two loops that are linked to each other.

Figure 2A:
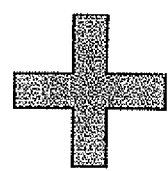
FIGS. 2A, 2B, 2C, 2D, 2E and 2F are schematic plan views of metal structures having various different profiles that can be used for embodiments of the present invention.
Figure 2B:
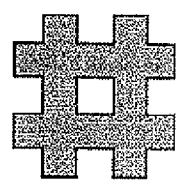
Figure 2C:
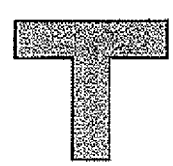
Figure 2D:
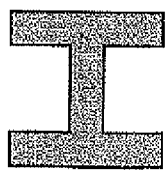
Figure 2E:
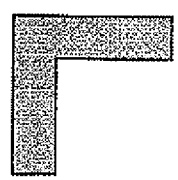
Figure 2F:
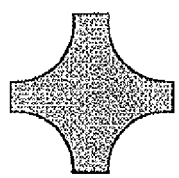

Examples of plane profiles of metal structures having a crossing section include those illustrated in FIGS. 2A and 2B, in each of which one or more than one intersections are formed at least by two belt-shaped sections. FIGS. 2C through 2E show examples where at least one of the belt-shaped sections is terminated at an intersection and hence does not project to the other side. FIG. 2F shows an example having a single intersection and the angles of intersection are not sharp but rounded because of the manufacturing method thereof. The intersection of belt-shaped sections may not necessarily produce rectangles. While belt-shaped sections extend straight in the instances of FIGS. 2A through 2F, they may alternatively extend to show a curved profile.

Materials that can be used for forming a metal structure for the purpose of this embodiment include gold, silver, cupper, aluminum and alloys of any of them. A metal structure may be formed on a base with a thin film of chromium or titanium interposed between them from the viewpoint of tight adhesion to the base.

A metal structure is made to have a film thickness between about 10 nm and about 100 nm.

Figure 18A:
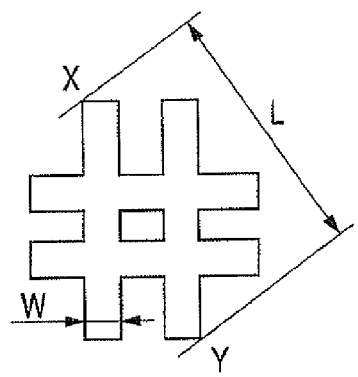
FIGS. 18A and 18B are schematic illustrations of principles for gauging the size of the plane pattern of a metal structure that can be used for embodiments of the present invention.
Figure 18B:
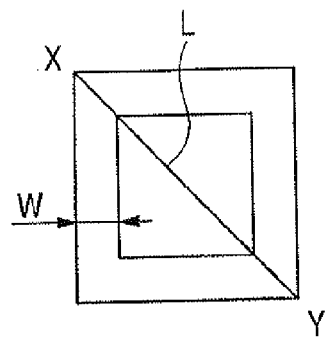

The plane size of a metal structure, or the largest distance as observed between two arbitrarily selected points along the outer periphery of a metal structure is preferably within a range between 10 nm and 1,450 nm and more preferably between 50 nm and 450 nm. In the case of a pattern of projecting parallels as illustrated in FIG. 18A, the distance between points X and Y is longest and hence this distance is preferably found within the above defined range. Similarly, in the case of a square ring pattern as illustrated in FIG. 18B, the length of diagonal line L between points X and Y on the outer periphery is longest and hence this length is preferably found within the above defined range. In the case of a circular ring pattern as illustrated in FIG. 1C, the diameter of the outer circle is preferably found within the above defined range. It is possible to highly effectively obtain localized surface plasmon resonance for realizing the aimed detection sensitivity when the size of the plane profile of the metal structure is found within the above-defined range.

On the other hand, a metal structure is formed basically as one or more than one belt-shaped sections. The width (belt width) of the belt-shaped sections is not subjected to any particular limitations so long as they can be used to form a metal structure and obtain localized surface plasmon resonance at which the present invention is aimed, although the belt width is preferably within a range between 10 nm and 100 nm. In the case of a circular ring pattern as illustrated in FIG. 1C, the belt width is the difference in radius between the outer peripheral circle and the inner peripheral circle. In the case of patterns as illustrated in FIGS. 18A and 18B, the belt width of the patterns is the distance indicated by W. The widths of the belt-shaped sections may be the same and identical throughout the metal structure or some of them may differ from others.

If necessary, two or more than two metal structures are arranged on a base. When a plurality of metal structures are arranged, the gap separating any two adjacently located metal structures is preferably between 50 nm and 2,000 nm, more preferably between 150 nm and 1,000 nm, because the distribution and the intensity of the spatial electric field are influenced by the interaction of the metal structures due to surface plasmon. If, on the other hand, the gap separating any two adjacently located metal structures is too large, the density of the metal structures is reduced to by turn reduce the signal intensity so that a specifically designed optical system may have to be introduced. Therefore, it is desirable that the gap separating any two adjacently located metal structures is found within the above-defined range.

Figure 3:
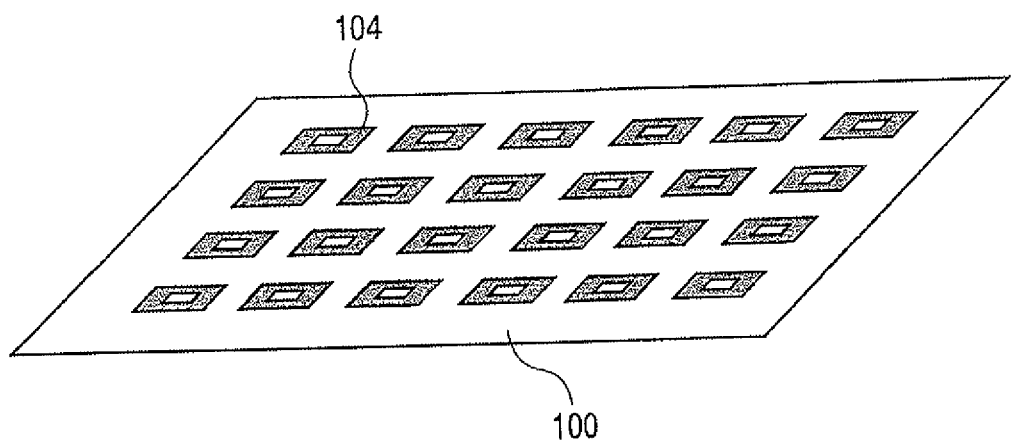
FIG. 3 is a schematic perspective view of an embodiment of detection element according to the present invention.
Figure 4:
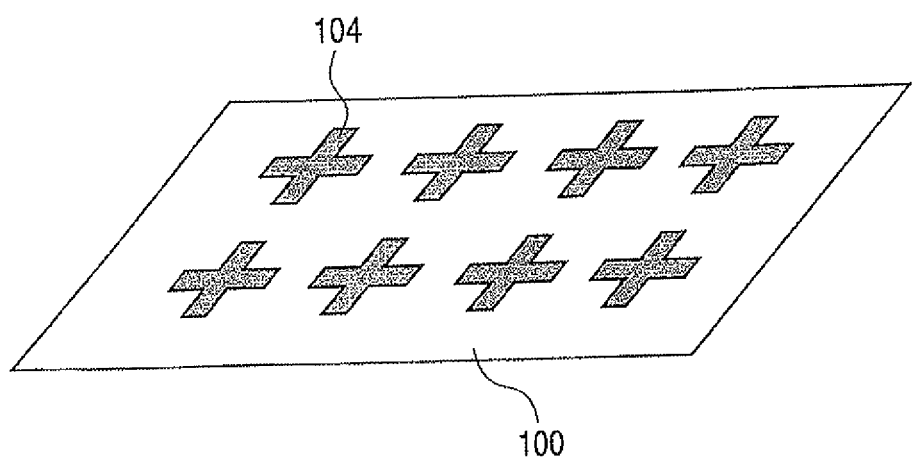
FIG. 4 is a schematic perspective view of another embodiment of detection element according to the present invention.

When two or more than two metal structures are arranged on a base, they may be differentiated from each other in terms of at least either of the plane profile and the size. When the efficiency of manufacturing metal structures and the simplicity of the configuration of the detection system are taken into consideration, it is preferable that metal structures having the same profile and the same size are regularly arranged in array within a region of a rectangle of several millimeters as shown in FIGS. 3 and 4. With such an arrangement, it is possible to observe transmitted light, scattered light and reflected light with ease. In FIGS. 3 and 4, reference symbol 100 denotes a base and reference symbol 104 denotes a metal structure.

Since the film thickness, the outer profile, the belt width and the gap separating any two adjacently located metal structures affect the peak position of the localized surface plasmon resonance spectrum, the metal structures need to be formed to a size that is suitable for measuring operations. The detection sensitivity of a detection element according to the present invention is improved when the plane profile of the metal structure or structures is made to have a loop section and/or a crossing section probably for the following reasons. First, the length of contour of a metal structure is increased. Second, the number of corners of a metal structure is increased when a crossing section is used. Third, the distance between edges of the plane profile of a metal structure is reduced. These reasons may be combined to provide synergetic effects. The length of contour of the metal structure is defined only by the outer periphery when the profiles of FIGS. 1A through 1C do not have a hollow space (blank part), On the other hand, the length of contour of the metal structure is increased because it is the sum of the length of the outer periphery and that of the inner periphery when they have a hollow space as actually shown in FIGS. 1A through 1C. Additionally, the total number of corners of the profile of FIG. 1A is eight, which is twice of the total number of corners of the profile when it does not have a hollow space and has four corners. Furthermore, when the profile of FIG. 1A does not have the hollow space H, the distance between two points on the edges E1 that define the outer periphery (inter-edge distance) is smallest for two oppositely disposed sides of the square. When, on the other hand, the profile of FIG. 1A has the hollow space H, the inter-edge distance is defined by the distance between an edge E1 of the outer periphery and the corresponding edge E2 of the inner periphery. In other words, the inter-edge distance is reduced in the metal structure having the hollow space H if compared with the inter-edge distance of the metal structure having not hollow space H, although the two metal structures have the same size.

In the case of a ring-shaped profile as shown in FIG. 1C, the length of contour is the sum of the outer periphery and the inner periphery so that the surface surface plasmon intensifying regions of the edges are extended. Additionally, the inside and the outside of the ring are arranged close to each other so as to allow surface plasmon to interact with each other. Thus, this arrangement can be expected to show an effect of further intensifying the overall surface plasmon.

On the other hand, an H-shaped metal structure having crossing sections as shown in FIG. 2D provides an increased length of contour and a shorter inter-edge distance if compared with a metal structure having a square profile (without any hollow space) of the same size and hence not having any crossing section. Additionally, the number of corners is raised to twelve if compared with a metal structure having a solid square profile whose number of corners are four. A metal structure having such a profile also shows a large surface plasmon intensifying region and an increased ratio of the effective detection region. Additionally, the closely located surface plasmon interact with each other at each of the corners and the intersections to further intensify the overall surface plasmon.

In an experiment, the inventors of the present invention cut a square metal pattern of a size of 100 nm×100 nm into fine pieces of a size of 10 nm×10 nm in order to increase the number of edges and arranged them on a base to find that the effect of boosting the detection sensitivity to be obtained by the present invention is hardly obtainable with such an arrangement.

A glass plate, a quartz plate, a resin plate of polycarbonate, polystyrene or the like or an ITO substrate may be used for the base on which a metal structure is to be formed so long as such a plate is optically transparent and can be used for detecting the target substance by means of surface plasmon resonance.

Figure 5A:
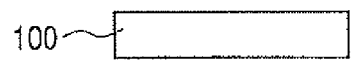
FIGS. 5A, 5B, 5C, 5D, 5E and 5F are schematic side views of an embodiment of detection element according to the present invention, illustrating different preparation steps thereof.
Figure 5B:
Figure 5C:
Figure 5D:
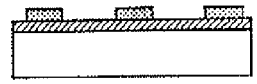
Figure 5E:
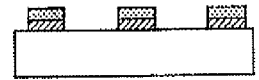
Figure 5F:
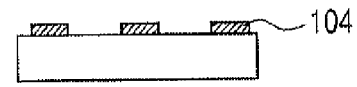

A target substance detection element of this embodiment can be obtained by forming a metal structure at a predetermined position on a base and arranging a capturing body on the metal structure. FIGS. 5A through 5F schematically illustrate a method of manufacturing a target substance detection element of this embodiment. Referring to FIGS. 5A through 5F, firstly a metal thin film 102 is formed on a base 100 (FIG. 5A) by sputtering or deposition (FIG. 5B). Then, a film of electron beam resist 103 is formed thereon by spin coating (FIG. 5C) and exposed to electron beam by means of an electron beam lithography system to obtain a developed resist pattern (FIG. 5D). Subsequently, the unnecessary parts of the metal thin film are etched out (FIG. 5E) and the resist is removed to produce metal structures 104 arranged in array (FIG. 5F). A focused ion beam system, an X-ray lithography system or an EUV lithography system may be used in place of an electron beam lithography system for patterning.

Figure 6A:
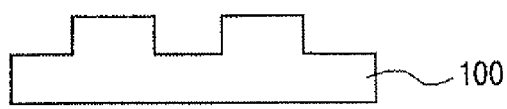
FIGS. 6A, 6B and 6C are schematic side views of another embodiment of detection element according to the present invention, illustrating different preparation steps thereof.
Figure 6B:
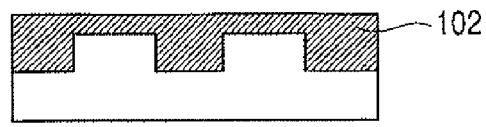
Figure 6C:
Figure 7A:
FIGS. 7A, 7B and 7O are schematic side views of still another embodiment of detection element according to the present invention, illustrating different preparation steps thereof.
Figure 7B:
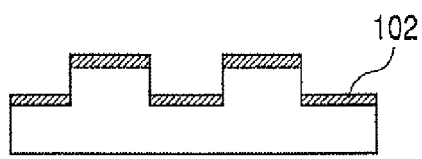
Figure 7C:
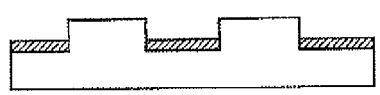

A target substance detection element of this embodiment can also be prepared by using a base 100 (FIG. 6A) having fine undulations and prepared by molding as schematically illustrated in FIGS. 6A through 6C. With this technique, a metal thin film 102 is formed on such a base 100 by sputtering or deposition (FIG. 6B). Then, the metal film on the surface is polished to produce desired metal structures on the base (FIG. 6C). FIGS. 7A through 7C schematically illustrate a method of preparing a target substance detection element of this embodiment where the metal thin film 102 is thinner than the depth of the undulations of the base 101. In this case, the projections of the base 100 may be located above the surface of the metal thin film 102 and the metal thin film 102 may be formed on the wall surfaces of the undulations. The unnecessary parts of the metal film may be removed by means of the etching back effect of a dry etching process instead of polishing.

Figure 8:
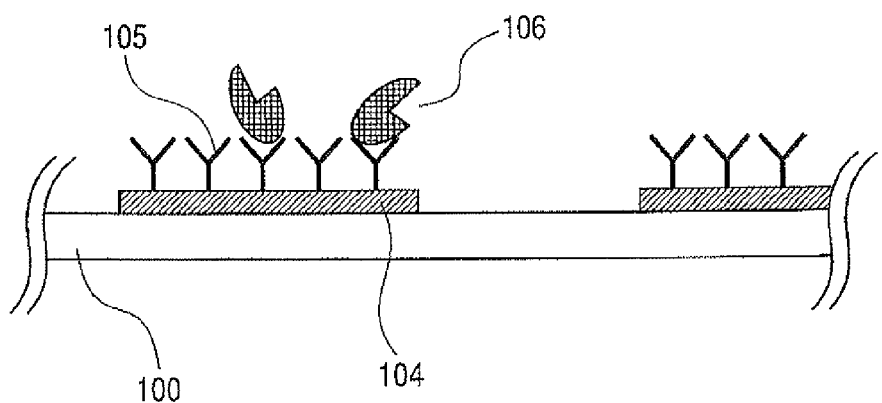
FIG. 8 is a schematic side view of a capturing body arranged on an embodiment of detection element according to the present invention.

When providing the element with a target substance capturing ability, it is preferable to use a chemical substance such as antibody 105 as capturing body for capturing the target substance 106 as shown in FIG. 8. As the antibody 105 is fixed to the metal structures 104, hybrid bodies are formed specifically when the target substance comes close to the metal structures to change the permittivity (refractive index) of the surface of the element. The antibody may be a member of an arbitrarily selected class of immunoglobulin, although the use of a derivative of the IgG class is preferable for the purpose of the present invention. The antibody that operates as capturing bodies may be antibody fragments produced by means of an appropriate technique. For the purpose of the present invention, the term "antibody fragments" refers to molecules or hybrid bodies that are smaller than the whole length of the antibody or the immunoglobulin. Preferably, the antibody fragments hold an essential part of the specific binding ability of the whole length antibody. Examples of antibody fragments that can be used for the purpose of the present invention not limitatively include Fab, Fab', F(ab')2, scFv, Fv, multi-specific multivalent antibodies (diabodies, triabodies, etc.) and Fd fragments. The use of antibody fragments makes it possible to capture the target substance at positions closer to the detection element and hence it is possible to improve the detection sensitivity. When a multi-specific multivalent antibody is used, it is possible to fix the capturing bodies onto the detection element easily and efficiently because it has a specific recognition ability relative to both the detection element and the target substance. Examples of hybrid bodies include those formed by an enzyme and a substrate and those formed by a complementary base pair produced by hybridization of DNA besides the above-described antibodies. Thus, one of the components of such a hybrid body can be utilized as capturing body for the other. Such capturing bodies are fixed to the surface of the detection element by a physical or chemical technique. Preferably, the surface of the element is coated with skim milk, casein, bovine serum albumin, phospholipid, polyethylene glycol or any of the derivatives thereof to eliminate signals from non-specific adsorption of co-existing impurities.

(Second Embodiment)

Now, the second embodiment will be described below.

The substrate of the second embodiment comprises a base and a metal film formed on the surface of the base. The metal film has apertures and the profile of the apertures has at least either of a loop section and a crossing section. A target substance detection element can be obtained as target substance capturing bodies are fixed to the metal film of the substrate.

The apertures of the substrate of the second embodiment include those having at least one or more than one intersections of belt-shaped apertures. A target substance detection element can be obtained by fixing target substance capturing bodies to the metal film of the substrate.

The element shows an improved detection sensitivity for detecting a target substance as the arrangement of apertures of the metal film is optimized and the plane profile of the apertures (metal pattern) is made to show a specific shape. The term "plane profile" of aperture as used herein refers to the profile thereof on a plane running in parallel with the substrate surface (base surface) and hence the profile in the plan view of the substrate surface as viewed from above.

In this embodiment according to the present invention, the plane profile of the aperture of a metal film has at least either of a loop section and a crossing section. FIGS. 19A through 19F illustrate schematic plan views of metal films (profiles of apertures) having one or more than one crossing sections.

Figure 19A:
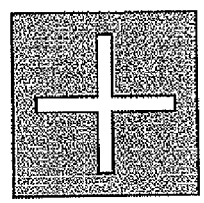
FIGS. 19A, 19B, 19C, 19D, 19E and 19F are schematic plan views of various different metal film apertures that can be used for embodiments of the present invention.
Figure 19B:
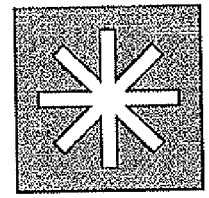
Figure 19C:
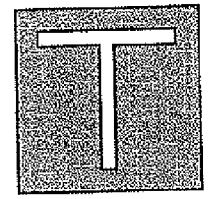
Figure 19D:
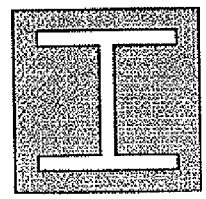
Figure 19E:
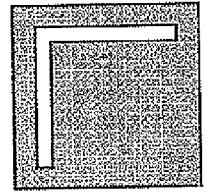
Figure 19F:
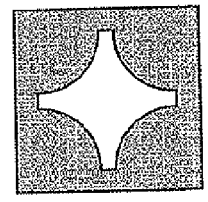

Plane profiles of apertures of metal films that can be used for this embodiment include those illustrated in FIGS. 19A and 19B, in each of which an intersection is formed at least by two belt-shaped apertures, and those illustrated in FIGS. 19C through 19E, in each of which at least one of the belt-shaped apertures is terminated at the intersection thereof and hence does not project to the other side. FIG. 19F shows an example having a single intersection and the angles of intersection are not sharp but rounded because of the manufacturing method thereof. The intersection of belt-shaped apertures may not necessarily produce rectangles. While belt-shaped apertures extend straight in the instances of FIGS. 19A through 19F, they may alternatively extend to show a curved profile.

Figure 20A:
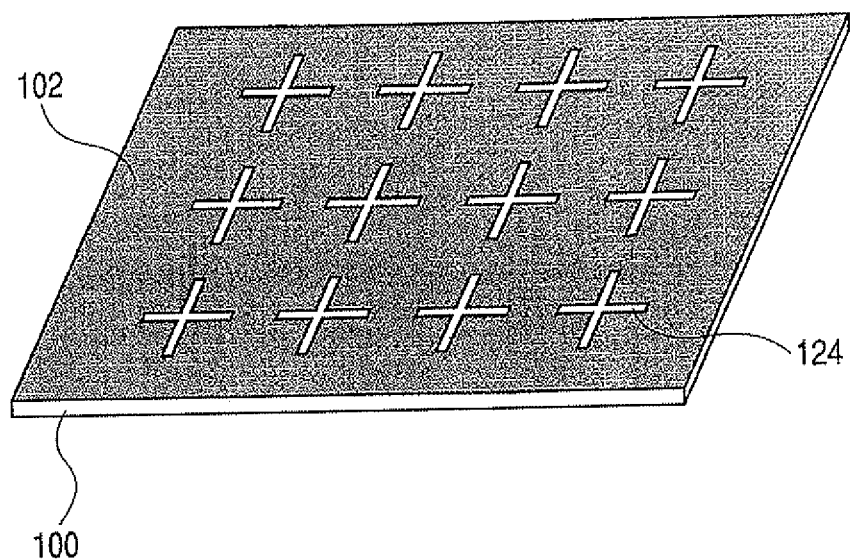
FIGS. 20A and 20B are schematic perspective views of different metal film apertures that can be used for embodiments of the present invention.

FIG. 20A shows a substrate formed by arranging a metal film 102 having apertures with crossing sections that are a plurality of cross apertures 124 on a base 100. The apertures 124 of FIG. 20A may alternatively be made to show a profile as shown in any of FIGS. 19B through 19F.

Figure 20B:
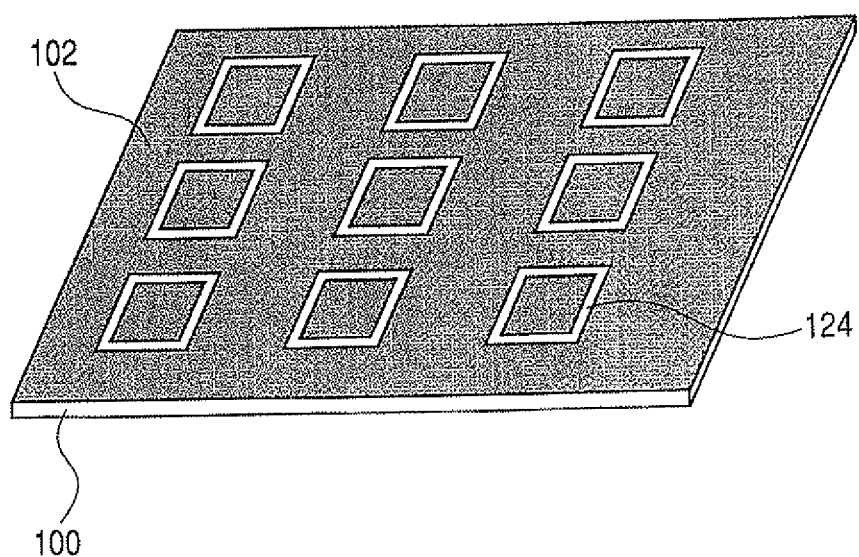

FIG. 20B shows a substrate formed by arranging a metal film 102 having apertures with a plurality of loop sections on a base 100. The apertures of FIG. 20B may alternatively be made to show any other profile.

Materials that can be used for forming a metal film for the purpose of this embodiment include gold, silver, cupper, aluminum and alloys of any of them. A metal film may be formed on a base with a thin film of chromium or titanium interposed between them from the viewpoint of tight adhesion to the base.

A metal film is made to have a film thickness between about 10 nm and about 100 nm.

Figure 24:
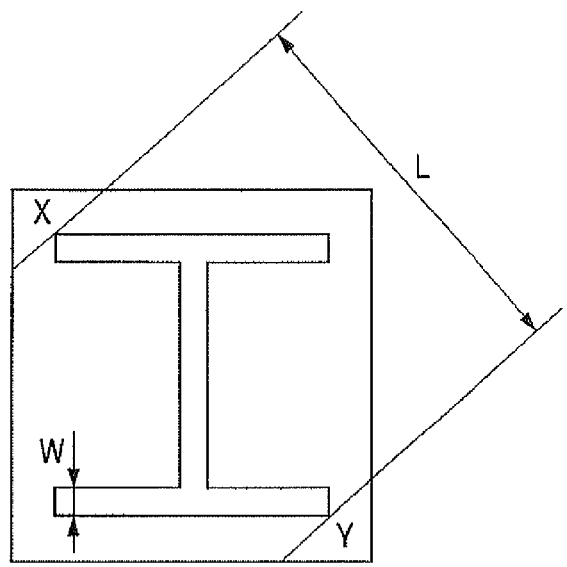
FIG. 24 is a schematic plan view of a small metal structure that can be used for embodiments of the present invention.

The term "largest length observed between two arbitrarily selected ends (the length between opposite ends)" of an aperture of a metal film as used herein refers to the one in a plane profile of the aperture. More specifically, it is the largest distance as observed between two arbitrarily selected points on the outer periphery, which is preferably within a range between 10 nm and 1,450 nm, more preferably within a range between 50 nm and 450 nm. In the case of a pattern as illustrated in FIG. 24, the distance L between points X and Y is longest and hence this distance is preferably found within the above defined range. It is possible to highly effectively obtain surface plasmon resonance for realizing the aimed detection sensitivity when the size of the plane profile of the aperture is found within the above-defined range.

On the other hand, each of the apertures of a metal film is formed basically as one or more than one belt-shaped sections. The width (belt width) of the belt-shaped sections is not subjected to any particular limitations so long as they can be used to form an aperture and obtain surface plasmon resonance at which the present invention is aimed, although the belt width is preferably within a range between 10 nm and 100 nm because such a belt width provides an absorption spectrum intensity that facilitates the observation. The widths of the belt-shaped apertures may be the same and identical throughout the metal film or some of them may differ from others.

If necessary, two or more than two apertures are arranged in the metal film on a base. When a plurality of apertures are arranged, the gap separating any two adjacently located apertures is preferably between 50 nm and 2,000 nm, more preferably between 150 nm and 1,000 nm, because the distribution and the intensity of the spatial electric field are influenced by the interaction of surface plasmon at the apertures. If the gap separating any two adjacently located apertures is too large, the area of the apertures is reduced to by turn reduce the signal intensity so that a specifically designed optical system may have to be introduced. Therefore, it is desirable that the gap separating any two adjacently located apertures is found within the above defined range.

When two or more than two apertures are arranged in a metal film, they may be differentiated from each other in terms of at least either of the plane profile and the size. When the efficiency of manufacturing metal films and the simplicity of the configuration of the detection system are taken into consideration, it is preferable that apertures having the same profile and the same size are regularly arranged in array within a region of a rectangle of several millimeters as shown in FIGS. 20A and 20B. With such an arrangement, it is possible to observe transmitted light, scattered light and reflected light with ease.

Since the film thickness of the metal film and the outer profile and the belt width of the apertures as well as the gap separating any two adjacently located apertures affect the peak position of the surface plasmon absorption spectrum, both the metal film and the apertures need to be formed to a size that is suitable for measuring operations. The detection sensitivity of a detection element of this embodiment according to the present invention is improved when the plane profile of the aperture or each of the apertures is made to have one or more than one intersections because the length of contour of an aperture is increased and the number of corners is increased when one or more than one intersections are formed.

When an H-shaped aperture having crossing sections as illustrated in FIG. 19D is compared with a square aperture of the same size that does not have any crossing section, the length of contour of the former aperture is increased and the distance separating oppositely disposed edges is decreased. Additionally, the total number of corners of the profile of such an aperture is twelve, whereas that of the profile of a square aperture is four. An aperture having such a profile also shows a large surface plasmon intensifying region and an increased rate of the effective detection region. Additionally, closely located surface plasmon interact with each other at each of the corners and the intersections to further intensify the overall surface plasmon.

A glass plate, a quartz plate, a resin plate of polycarbonate, polystyrene or the like or an ITO substrate may be used for the base on which a metal film is to be formed so long as such a plate can be used for detecting the target substance by means of surface plasmon resonance.

Figure 21A:
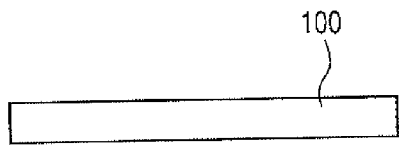
FIGS. 21A, 21B, 21C, 21D, 21E and 21F are schematic side views of still another embodiment of detection element according to the present invention, illustrating different preparation steps thereof.
Figure 21B:
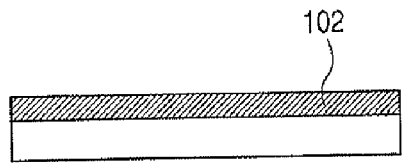
Figure 21C:
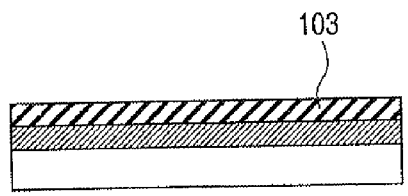
Figure 21D:
Figure 21E:
Figure 21F:
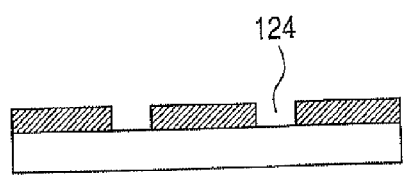

A target substance detection element of this embodiment can be obtained by forming apertures in a metal film at a predetermined position on a base and arranging capturing bodies on the metal film. FIGS. 21A through 21F schematically illustrate a method of manufacturing a target substance detection element of this embodiment. Referring to FIGS. 21A through 21F, firstly a metal thin film 102 is formed on a base 100 (FIG. 21A) by sputtering or deposition (FIG. 21B). Then, a film of electron beam resist 103 is formed thereon by spin coating (FIG. 21C) and exposed to light by means of an electron beam lithography system to obtain a developed resist pattern (FIG. 21D). Subsequently, the unnecessary parts of the metal thin film are etched out (FIG. 21E) and the resist is removed to produce apertures 124 arranged in array (FIG. 21F). A focused ion beam system, an X-ray lithography system, an EUV lithography system or an excimer laser lithography system may be used in place of an electron beam lithography system for patterning.

Figure 22:
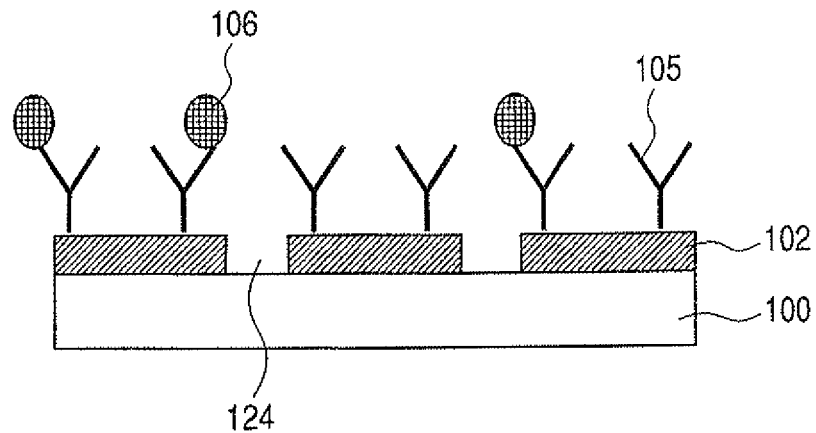
FIG. 22 is a schematic side view of a capturing body arranged on an embodiment of detection element according to the present invention.

When providing the element with a target substance capturing ability, it is preferable to use a chemical substance such as antibody 105 as capturing body for capturing the target substance 106 as shown in FIG. 22. The description made above on antibodies 105 by referring to FIG. 8 is also applicable to this embodiment.

(Third Embodiment)

Now, the third embodiment will be described below. The substrate of the third embodiment is a substrate of a target substance detection element comprising a complex structure formed by combining a base and a plurality of metal members arranged on the surface of the base. The complex structure includes an outer frame structure having an aperture and an inner structure arranged in the aperture and spatially separated from the outer frame structure.

An element (detection element) formed by using such a substrate is made to comprise at least a base and a complex structure arranged on the surface of the base to generate surface plasmon resonance. The element shows an improved detection sensitivity for detecting a target substance as the arrangement of the complex structure is optimized and the plane profile of the complex structure (metal pattern) is made to show a specific shape. The term "plane profile" of complex structure as used herein refers to the profile thereof on a plane running in parallel with the substrate surface (base surface) and hence the profile of the plan view of the substrate surface as viewed from above.

The metal pattern (complex structure) has a profile showing an outer structure that is a frame structure having an aperture (to be referred to as small metal structure hereinafter) and an inner structure, at least a part of which is located in the inside of the aperture (to be referred to as minute metal structure hereinafter). The metal pattern is formed by the outer profile of the small metal structure, the profile of the aperture of the small metal structure and that of the minute metal structure.

FIGS. 25A through 25F illustrate different outer profiles that can be used for the small metal structure, which is a component of the metal pattern of this embodiment.

Figure 25A:
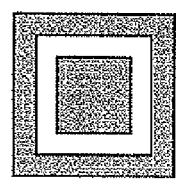
FIGS. 25A, 25B, 25C, 25D, 25E and 25F are schematic illustrations of principles for gauging the size of the plane pattern of metal film apertures.
Figure 25B:
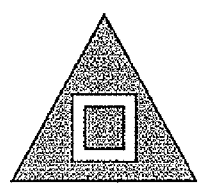
Figure 25C:
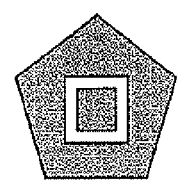
Figure 25D:
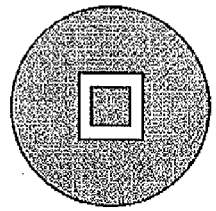
Figure 25E:
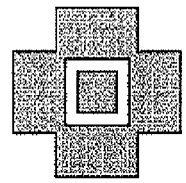
Figure 25F:
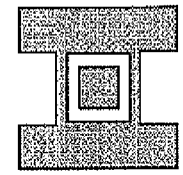

The pattern of the outer profile of the small metal structure can be a plane profile of film as shown in FIG. 25A, a polygonal profile selected from those illustrated in FIGS. 25B and 25C, a curved profile of a circle or an ellipse as shown in FIG. 25D, a cross-shaped profile as shown in FIG. 25E or an H-shaped profile as shown in FIG. 25F. The angles of intersection may not be sharp but rounded because of the manufacturing method thereof. The intersection may not necessarily produce rectangles.

FIGS. 26A through 26F illustrate different aperture profiles that can be used for the small metal structure, which is a component of the metal pattern of this embodiment.

Figure 26A:
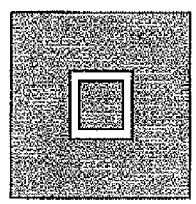
FIGS. 26A, 26B, 26C, 26D, 26E and 26F are schematic plan views of the apertures of small metal structures that can be used for embodiments of the present invention.
Figure 26B:
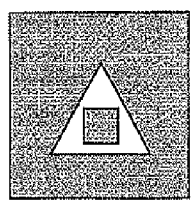
Figure 26C:
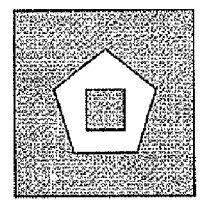
Figure 26D:
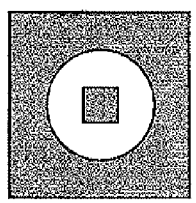
Figure 26E:
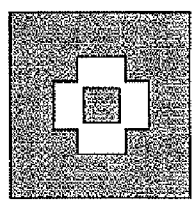
Figure 26F:
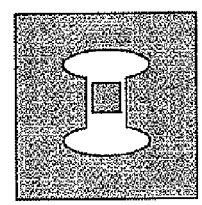

The pattern of the profile of the aperture profile of the small metal structure can be a polygonal profile selected from the those illustrated in FIGS. 26A, 26B and 26C, a curved profile of a circle or an ellipse as shown in FIG. 26D, a cross-shaped profile as shown in FIG. 26E or an H-shaped profile as shown in FIG. 26F. The angles of intersection may not be sharp but rounded because of the manufacturing method thereof. The intersection may not necessarily produce rectangles.

FIGS. 27A through 27F illustrate different profiles that can be used for the minute metal structure, which is a component of the metal pattern of this embodiment.

Figure 27A:
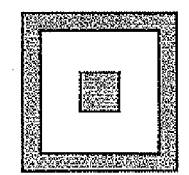
FIGS. 27A, 27B, 27C, 27D, 27E and 27F are schematic plan views of the various different contours of minute metal structures that can be used for embodiments of the present invention.
Figure 27B:
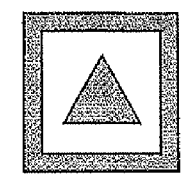
Figure 27C:
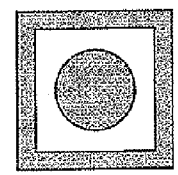
Figure 27D:
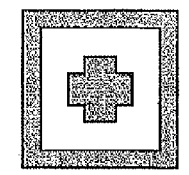
Figure 27E:
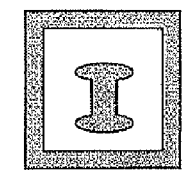
Figure 27F:
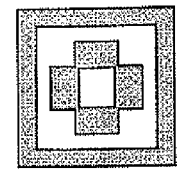

The profile of the minute metal structure can be a polygonal profile selected from the those illustrated in FIGS. 27A and 27B, a curved profile of a circle or an ellipse as shown in FIG. 27C, a cross-shaped profile as shown in FIG. 27D, an H-shaped profile as shown in FIG. 27E or a profile similar to that of the small metal structure having an aperture as shown in FIG. 27F. The angles of intersection may not be sharp but rounded because of the manufacturing method thereof. The intersection may not necessarily produce rectangles.

The pattern of the profile of the complex structure is realized by combining a profile selected from FIGS. 25A through 25F, a profile selected from FIGS. 26A through 26F and a profile selected from FIGS. 27A through 27F. FIGS. 28A through 28F illustrate examples of such profiles.

Figure 28A:
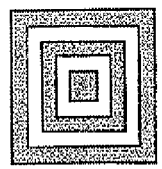
FIGS. 28A, 28B, 28C, 28D and 28E are schematic plan views of complex metal structures that can be used for embodiments of the present invention.
Figure 28B:
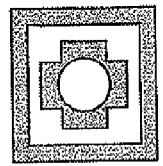
Figure 28C:
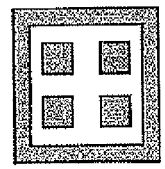
Figure 28D:
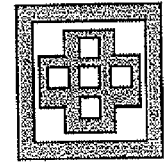
Figure 28E:
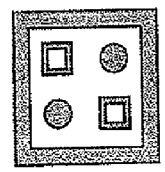

The pattern of the profile of the complex structure may be any of those illustrated in FIGS. 28A through 28E. FIG. 28A shows a pattern comprising a small metal structure having an outer aperture, a first minute metal structure arranged in the outer aperture and having an inner aperture, and a second minute metal structure arranged in the inner aperture. FIG. 28B shows a pattern formed by combining a small metal structure and a minute metal structure but the profile of the aperture of the small metal structure and that of the minute metal structure differ from each other. FIG. 28C shows a pattern formed by combining a small metal structure having a single aperture and a plurality of minute metal structures arranged in the aperture. FIG. 28D shows a pattern formed by combining a small metal structure and a minute metal structure provided with a plurality of apertures. FIG. 28E shows a pattern formed by combining a small metal structure having a single aperture and a plurality of minute structures that are different from each other and arranged in the aperture. The angles of intersection may not be sharp but rounded because of the manufacturing method thereof. The intersection may not necessarily produce rectangles.

Materials that can be used for forming a complex structure for the purpose of this embodiment include gold, silver, copper, aluminum and alloys of any of them. The small metal structure and the minute metal structure may be made of respective materials that are different from each other. A complex structure may be formed on a base with a thin film of chromium or titanium interposed between them from the viewpoint of tight adhesion to the base.

A complex structure is made to have a film thickness between about 10 nm and about 100 nm. The small metal structure and the minute metal structure may have respective film thicknesses that are different from each other.

Figure 29A:
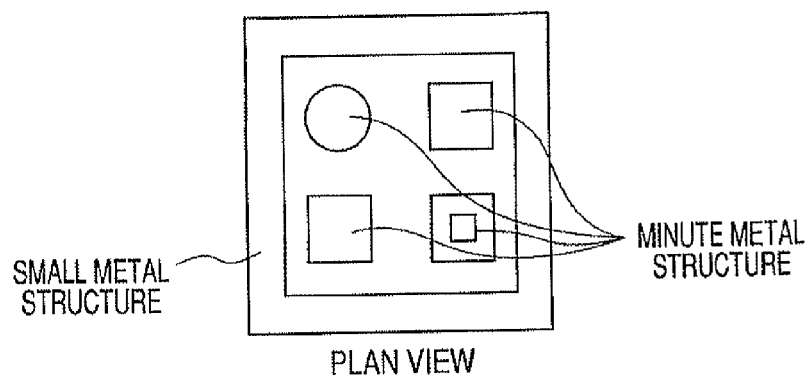
FIGS. 29A and 29B are schematic illustrations of a small metal structure of a embodiment of the present invention, showing a minute metal structure exists in the aperture thereof.
Figure 29B:
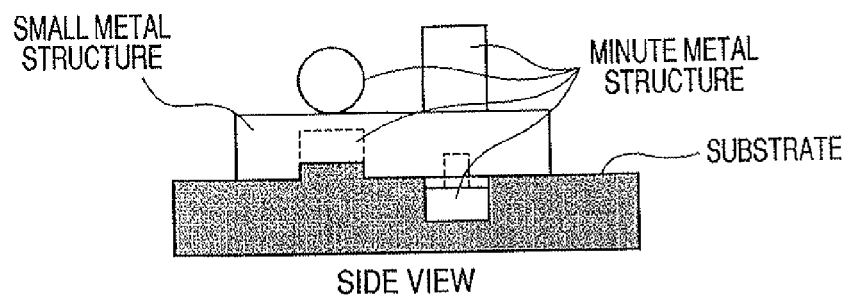

When the small metal structure and the minute metal structure are viewed in a horizontal direction, the minute metal structures are at least partly found or held in contact with the inside of the aperture space of the small metal structure as shown in FIG. 29B. While the small metal structure and the minute metal structures show a cubic or spherical form in FIGS. 29A and 29B, they may alternatively show a profile formed by combining one or more than one curved surfaces and one or more than one plane surfaces.

Figure 32A:
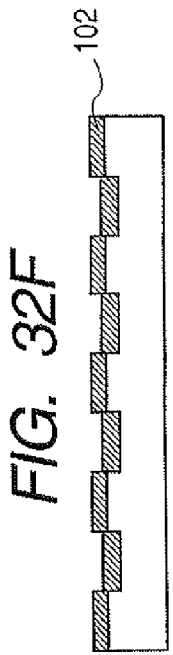
FIGS. 32A, 32B, 32C, 32D, 32E, 32F, 32G, 32H, 32I and 32J are schematic side views of still another embodiment of detection element according to the present invention, illustrating different preparation steps thereof.
Figure 32F:
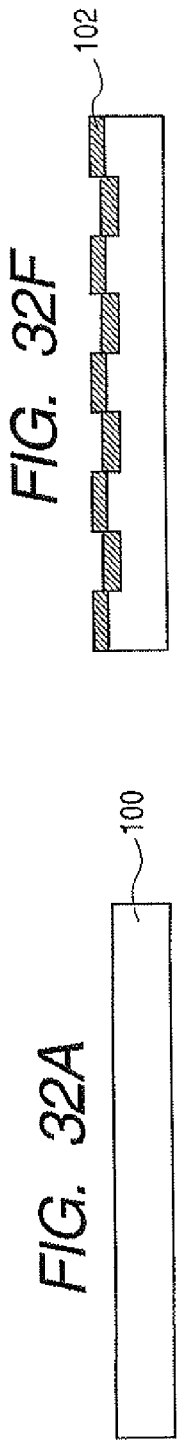
Figure 32B:
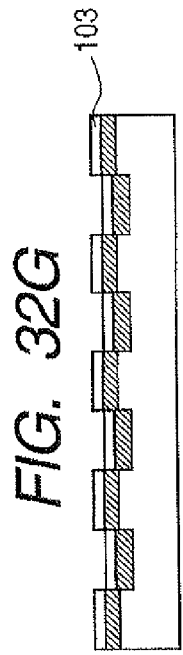
Figure 32G:
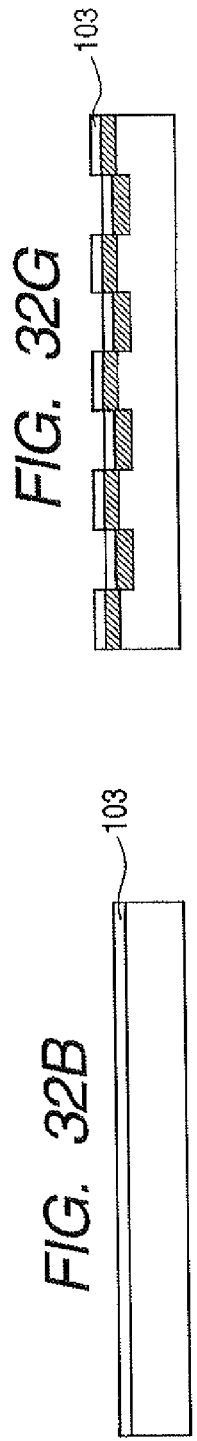
Figure 32C:
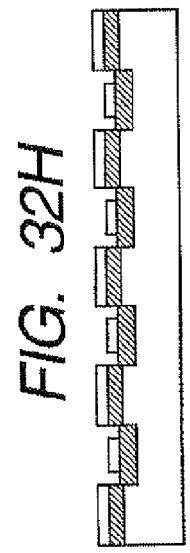
Figure 32H:
Figure 32D:
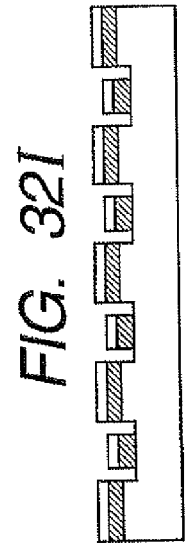
Figure 32I:
Figure 32E:
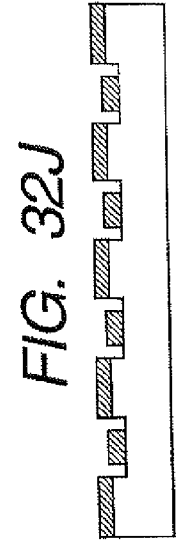
Figure 32J:

A target substance detection element as shown in FIGS. 29A and 29B can be obtained by forming a metal structure at a predetermined position on a base and arranging a capturing body on the metal structure. FIGS. 32A through 32J schematically illustrate a method of manufacturing a target substance detection element of this embodiment. Referring to FIGS. 32A through 32J, first a film of electron beam resist 103 is formed on a base 100 by spin coating (FIG. 32A) and exposed to electron beam by means of an electron beam lithography system to obtain a developed resist pattern (FIG. 32C). Subsequently, the base is subjected to an etching operation (FIG. 32D) to remove the resist and produce undulations on the base (FIG. 32E). Then, a metal thin film 102 is formed on the base having undulations by sputtering or deposition (FIG. 32F). Thereafter, a film of electron beam resist 103 is formed thereon by spin coating (FIG. 32G) and exposed to electron beam by means of an electron beam lithography system to obtain a developed resist pattern (FIG. 32H). Then, the unnecessary parts of the metal thin film are etched out (FIG. 32I) and the resist is removed to produce metal structures arranged in array (FIG. 32J). A focused ion beam system, an X-ray lithography system, an EUV lithography system or an excimer laser lithography system may be used in place of an electron beam lithography system for patterning.

The term or expression "outer profile" or "aperture" for the small metal structure or the term "largest length observed between two arbitrarily selected ends (length between opposite ends)" for the minute metal structure or each of the minute metal structures as used herein refers to the same in a plane profile of the aperture. More specifically, it is sufficient for the largest distance between two arbitrarily selected points on the outer periphery to be found within a specified range. In the case of a pattern as illustrated in FIG. 24, the distance L between points X and Y is longest and hence this distance is preferably found within the specified range. It is possible to highly effectively obtain surface plasmon resonance for realizing the aimed detection sensitivity when the size of the plane profile of each of the structures is found within the above defined range.

If necessary, two or more than two complex structures are arranged on a base. When a plurality of complex structures are arranged, the gap separating any two adjacently located complex structures is preferably between 50 nm and 2,000 nm, more preferably between 150 nm and 1,000 nm, because the distribution and the intensity of the spatial electric field are influenced by the interaction of the surface plasmon of the complex structures. If the gap separating any two adjacently located complex structures is too large, the metal area is reduced to by turn reduce the signal intensity so that a specifically designed optical system may have to be introduced. Therefore, it is desirable that the gap separating any two adjacently located complex structures is found within the above-defined range.

Figure 30:
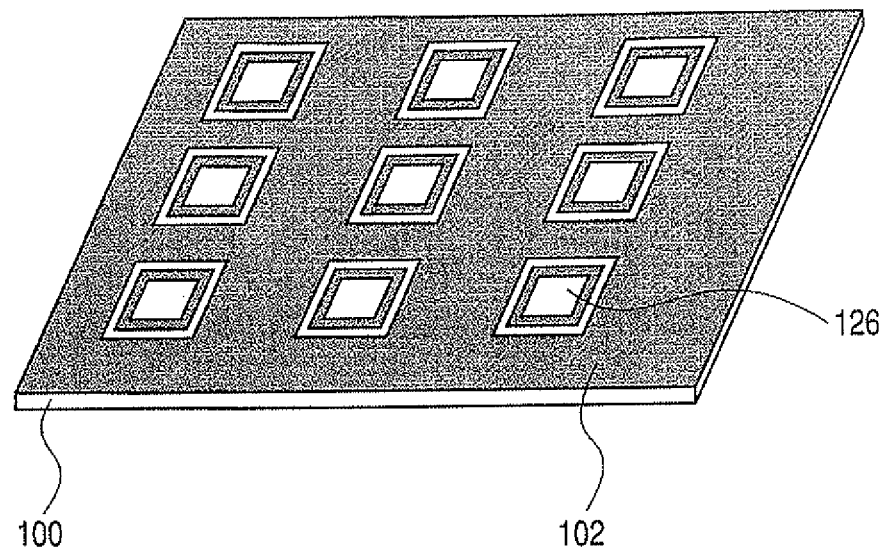
FIG. 30 is a schematic perspective view of an embodiment of detection element according to the present invention.

When two or more than two complex structures are arranged in a base, they may be differentiated from each other in terms of at least either of the plane profile and the size. When the efficiency of manufacturing complex structures and the simplicity of the configuration of the detection system are taken into consideration, it is preferable that complex metal structure apertures having the same profile and the same size are regularly arranged in array within a region of a rectangle of several millimeters as shown in FIG. 30. With such an arrangement, it is possible to observe transmitted light, scattered light and reflected light with ease.

Since the small metal structure and the minute metal structure or structures of a complex structure affect the peak position of the surface plasmon absorption spectrum, they need to be formed to a size that is suitable for measuring operations. The detection sensitivity of the combination of a small metal structure and one or more than one minute metal structures of this embodiment is improved when the minute metal structures arranged in the apertures of the small metal structures interact with each other.

A glass plate, a quartz plate, a resin plate of polycarbonate, polystyrene or the like or an ITO substrate may be used for the base on which a complex metal structure is to be formed so long as such a plate can be used for detecting the target substance by means of surface plasmon resonance.

When providing the element with a target substance capturing ability, it is preferable to use a chemical substance such as antibody 105 as capturing body for capturing the target substance 106 as shown in FIG. 22. The description made above on antibodies 105 by referring to FIG. 8 is also applicable to this embodiment.

II. Detection Apparatus and Detection Method

Now, a target substance detection apparatus comprising a detection element having a configuration as described above will be described below. A detection apparatus according to the present invention comprises at least a holding means for holding a detection element as defined above and a detecting means for detecting the signal from the element.

A detecting means comprising an optical detection system that includes a light source, a spectroscope and lenses, a reaction well for providing a reaction region to be used for moving a specimen to the element and causing it to react with the element and a liquid feed system that includes a flow channel and a liquid feed mechanism can suitably be used for the purpose of the present invention. A light source that can cover a wavelength range from the wavelengths of visible light to those of near infrared rays can suitably be used for the purpose of the present invention. For optical measuring operations, an absorption spectrum, a transmission spectrum, a scattering spectrum or a reflection spectrum can be used. Most preferably, a peak wavelength or the absorption intensity at a peak wavelength of an absorption spectrum is utilized. As the target substance is specifically bound to a capturing body arranged on the metal structure of the element, the localized surface plasmon resonance changes from the one that appears in an uncoupled state. Then, the peak wavelength of the absorption spectrum is shifted to the long wavelength region and the absorption intensity is raised. The quantity of the target substance can be determined from the calibration curve for the target substance that is prepared in advance and according to the extent of the shift. Since the element utilizes localized surface plasmon resonance, a phenomenon of local enhancement of electric field appears in the vicinity of the metal structure. This phenomenon can find applications in measuring methods such as surface enhanced Raman spectroscopy (SERS) and surface plasmon fluorescence spectroscopy (SPFS) and hence the target substance can be quantified by using any of such methods.

The holding means is to be used to hold or mount the detection element and can be selected appropriately from any means that can be used as component of the target substance detection apparatus.

The reaction region is a region for bringing the element and the specimen into contact with each other. As they react with each other, the target substance contained in the specimen comes to contact with the element to make it possible to detect the target substance.

Figure 9:
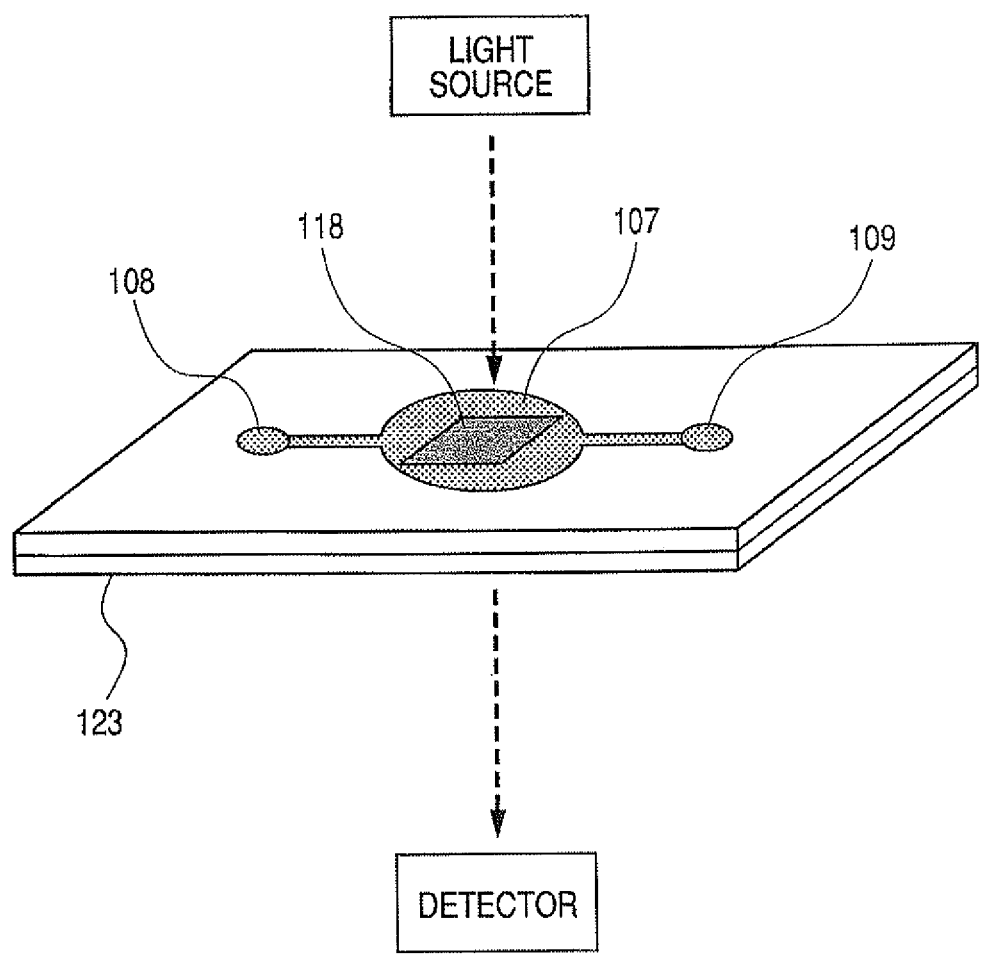
FIG. 9 is a schematic perspective view of an embodiment of detection apparatus according to the present invention.
Figure 10:
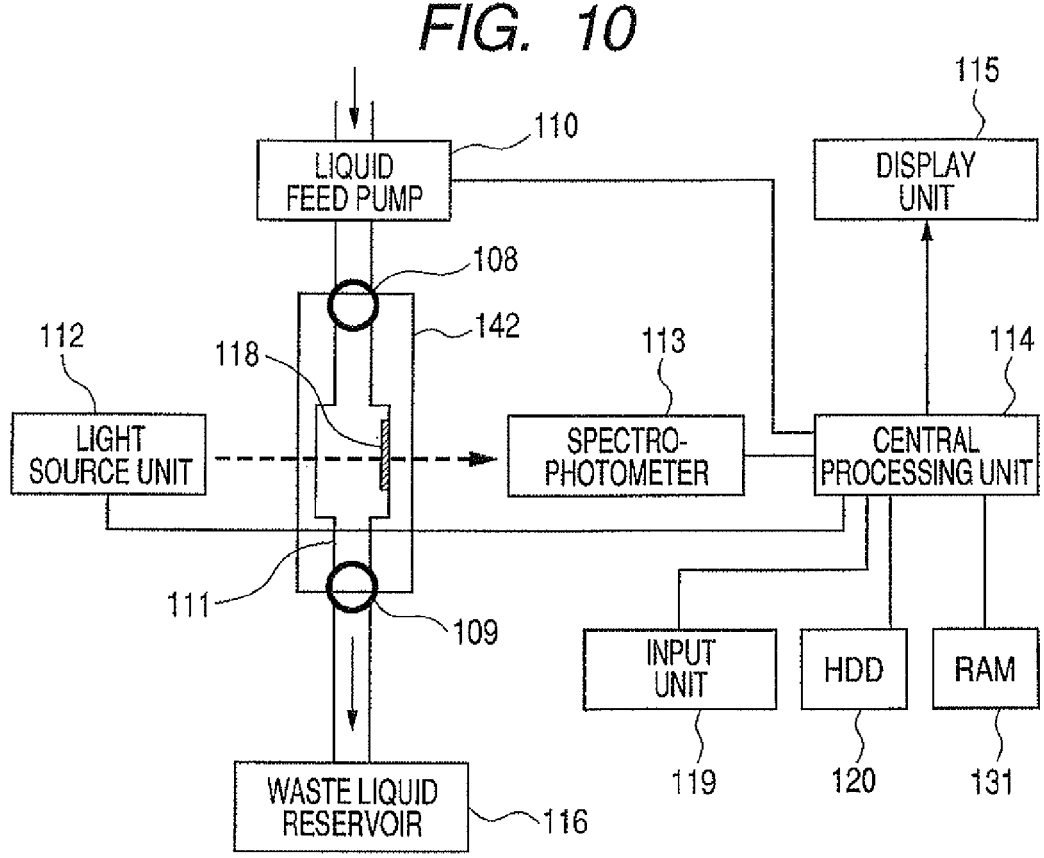
FIG. 10 is a schematic block diagram of an embodiment of detection apparatus according to the present invention.

A reaction well and a flow channel can be prepared with ease by means of a polydimethylsiloxane (PDMS) substrate that is popularly used in a so-called µTAS (micro total analysis system) type apparatus. A PDMS substrate is bonded to the substrate, on which the detection element is prepared, for use. A micro piston pump or a syringe pump may be used for the liquid feed mechanism. FIGS. 9 and 10 schematically illustrate a typical configuration of the apparatus. First, the element 118 is arranged in the reaction well 107 that operates both as element holding means and as reaction region forming means and a detection chip 142 having an inlet 108 and an outlet 109 is connected to a liquid feed pump 110 and a waste liquid reservoir 116. Then, the specimen that contains the target substance is introduced through the inlet 108 by means of the liquid feed pump 110. The specimen is subjected to an incubation process for a predetermined period of time and subsequently, light is transmitted through the reaction well 107 by means of the light source unit 112 to observe the transmission spectrum of the specimen by means of a spectrophotometer 113. The data obtained by the observation is compared with the calibration data prepared in advance by means of a central processing unit 114 and the results of the observation including the concentration of the target substance are displayed on the display unit 115. If necessary, before the observation, a phosphate buffer solution or the like is introduced by way of the inlet 108 as a cleaning liquid to clean the reaction well 107. It is possible to statically observe the change in the spectrum after a predetermined period of time and also dynamically observe the change on a real time basis. Then, the rate of change with time can be obtained as additional information. The above described operation procedure is input by way of the input unit 119 and the program that is stored in an HDD 120 in advance is loaded into a RAM 131 to execute the operation.

III. Detection Kit

A target substance detection kit according to the present invention is formed by using an element having the above-described configuration and a reagent necessary for capturing the target substance into the element, or an element having the above-described configuration, a detection apparatus having the above described configuration and a reagent necessary for capturing the target substance. An example of reagent necessary for capturing the target substance is an antibody. A reagent containing both an antibody and BSA (bovine serum albumin) etc. for preventing non-specific adsorption of antibody may also be used. Such a reagent is preferably held in a dry state.

Target substances that can suitably be captured by a detection kit according to the present invention include biosubstances (proteins, nucleic acids, sugar chains, lipids), allergens, bacteria and viruses. Additionally, a detection apparatus according to the present invention can be used as biosensor for medical use, industrial use and home use when a substance originating from a living body or a similar substance is used as component of the capturing body. Then, it is possible to detect a very minute quantity of the target substance contained in the specimen.

Now, the present invention will be described further by way of examples, although the present invention is by no means limited to the examples as described below.

EXAMPLE 1

Figure 11:
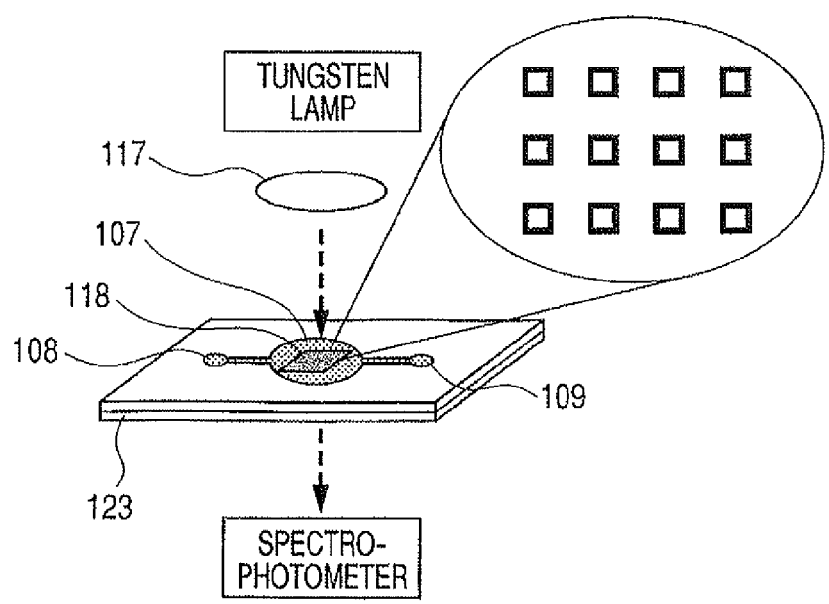
FIG. 11 is a schematic perspective view of the detection apparatus used in Examples 1 and 3.

FIG. 11 schematically illustrates the structure of the detection apparatus used in this example. The detection element 118 was prepared by forming a 20 nm-thick gold thin film on a 625 μm-thick quartz plate and patterning it to show a predetermined pattern by means of an electron beam lithography system. In FIG. 11, reference symbol 107 denotes a reaction well in which the detection element is arranged and reference symbol 108 denotes an inlet for introducing a specimen that contains the target substance, while reference symbol 109 denotes an outlet for delivering the specimen. Reference symbol 123 denotes a chip that comprises the reaction well 107, the inlet 108 and the outlet 109 and reference symbol 117 denotes a collimating lens.

Figure 12:
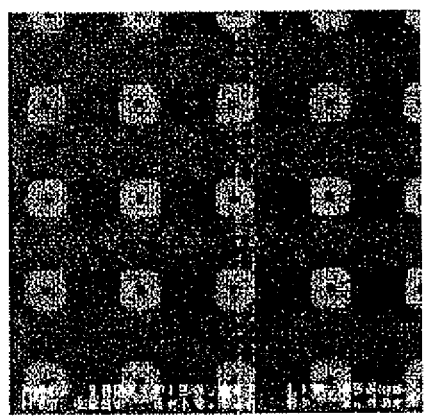
FIG. 12 is a schematic illustration of an SEM image obtained by the detection element of Example 1.

FIG. 12 is an image of the detection element obtained by means of a scanning electron microscope (SEM). As shown, the plane outer profile of each metal structure is a square with dimensions of 160 nm×160 nm and the belt width of each ring is 70 nm. It is not necessarily always possible to prepare the inside aperture so as to show a same profile as the outer profile of the metal structure because of the level of resolution. The patterns are spaced apart by a distance of 250 nm and arranged in array in a region of 3 mm×3 mm. The absorption spectrum of the structures of this example shows a peak wavelength at or near 800 nm.

Now, the method of fixing anti-AFP (α-fetoprotein) antibody, which is the target substance capturing body of this example, to the surface of the metal structure in order to provide the surface of the metal structure with a capturing ability will be described below. An ethanol solution of 11-mercaptoundecanoic acid that has a thiol group showing a strong affinity for gold, the material of the structure of this embodiment, is dropped on the element by means of a spotter to modify the surface of the structure. As a result, the carboxyl group is exposed on the surface of the structure. Under this condition, an aqueous solution of N-hydroxysulfosuccinimide (available from DOJINDO) and also an aqueous solution of 1-ethyl-3-[3-(dimethylamino)propyl]carbodiimide hydrochloride (available from DOJINDO) are dropped into the reaction region also by means of a spotter. As a result, the succinimide group is exposed on the surface of the structure. Then, the surface of the structure is modified as streptavidin is bound to it. Thereafter, biotinated anti-AFP antibody is fixed to the structure.

It is also possible to prepare a plurality of pattern regions for so many detection elements and different antibodies are respectively fixed to them so as to detect the different target substances contained in a specimen on the same substrate. Such an arrangement can be realized by using different antibodies and conducting a fixing operation similar to the above described one.

The AFP concentration in the specimen can be specifically gauged by following the operation procedure shown below.

(1) The specimen containing the target substance of AFP is introduced into the prepared element by way of the inlet 8 to have the AFT captured on the structure.
(2) The specimen is discharged and a phosphate buffer solution is introduced by way of the inlet 8 to clean the inside of the reaction well 7.
(3) As the last step, the inside of the reaction well is filled with a phosphate buffer solution to observe the absorption spectrum of the gold structure.

Figure 13:
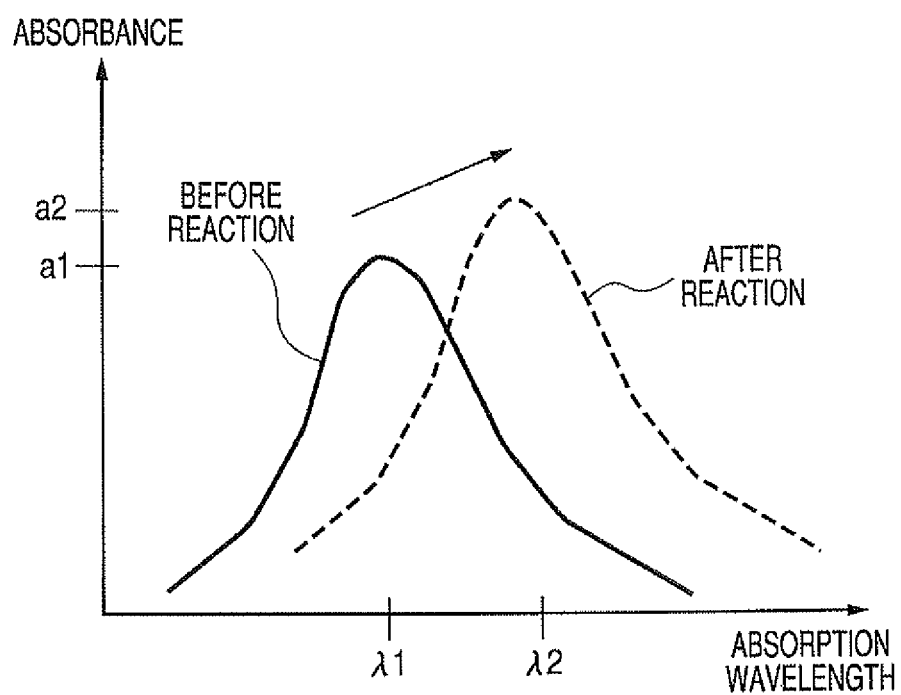
FIG. 13 is a graph illustrating the change in the detection spectrum (absorption spectrum) obtained in Example 1.

When the absorption spectrum is observed before and after the reaction, it will be found that a shift occurs to the absorption spectrum as shown in FIG. 13 as an example as the target substance is bound to the surface of the detection element due to a specific antigen-antibody reaction. The correlation of the peak intensity of the absorption spectrum or the extent of shift of the peak wavelength and the AFP concentration is determined in advance by means of a known AFP control solution so that it is possible to detect the minute AFP concentration of the specimen whose AFP concentration has not been known.

EXAMPLE 2

Figure 14:
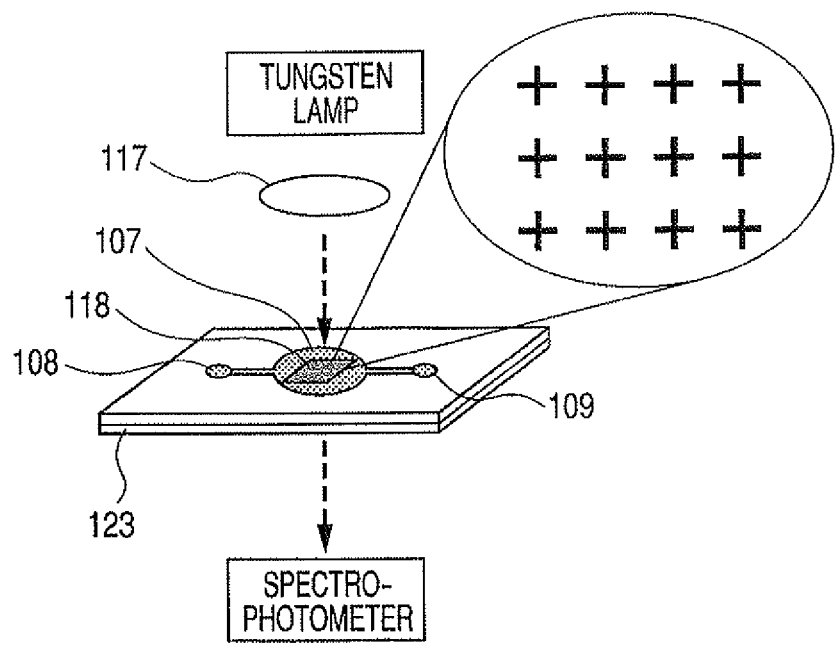
FIG. 14 is a schematic perspective view of the detection apparatus used in Example 2.

FIG. 14 schematically illustrates the structure of the apparatus used in this example. The detection element 118 was prepared by forming a 20 nm-thick gold thin film on a 625 μm-thick quartz plate and patterning it to show a predetermined pattern by means of an electron beam lithography system. When observed through a scanning electron microscope (SEM), the outer dimensions of the structure were 150 nm×150 nm and the line width was 50 nm. It is not necessarily always possible to prepare the intersections so as to show rectangles because of the level of resolution. The structures are spaced apart by a distance of 400 nm and arranged in array in a region of 3 mm×3 mm.

Now, the method of fixing anti-AFP (α-fetoprotein) antibody, which is the target substance capturing body of this example, to the surface of the gold structure in order to provide the surface of the structure with a capturing ability will be described below. An ethanol solution of 11-mercaptoundecanoic acid that has a thiol group showing a strong affinity for gold, the material of the structure of this embodiment, is dropped on the element by means of a spotter to modify the surface of the structure. As a result, the carboxyl group is exposed on the surface of the structure. Under this condition, an aqueous solution of N-hydroxysulfosuccinimide (available from DOJINDO) and also an aqueous solution of 1-ethyl-3-[3-(dimethylamino)propyl]carbodiimide hydrochloride (available from DOJINDO) are dropped into the reaction region also by means of a spotter. As a result, the succinimide group is exposed on the surface of the structure. Then, the surface of the structure is modified as streptavidin is bound to it. Thereafter, biotinated anti-AFP antibody is fixed to the structure.

It is also possible to prepare a plurality of pattern regions for so many detection elements and different antibodies are respectively fixed to them so as to detect the different target substances contained in a specimen on the same substrate. Such an arrangement can be realized by using different antibodies and conducting a fixing operation similar to the above described one.

The AFP concentration in the specimen can be specifically gauged by following the operation procedure shown below.
(1) The specimen containing the target substance of AFP is introduced into the prepared element by way of the inlet 108 to have the AFP captured on the structure.
(2) The specimen is discharged and a phosphate buffer solution is introduced by way of the inlet 108 to clean the inside of the reaction well 107.
(3) As the last step, the inside of the reaction well is filled with a phosphate buffer solution to observe the absorption spectrum of the gold structure.

Figure 15:
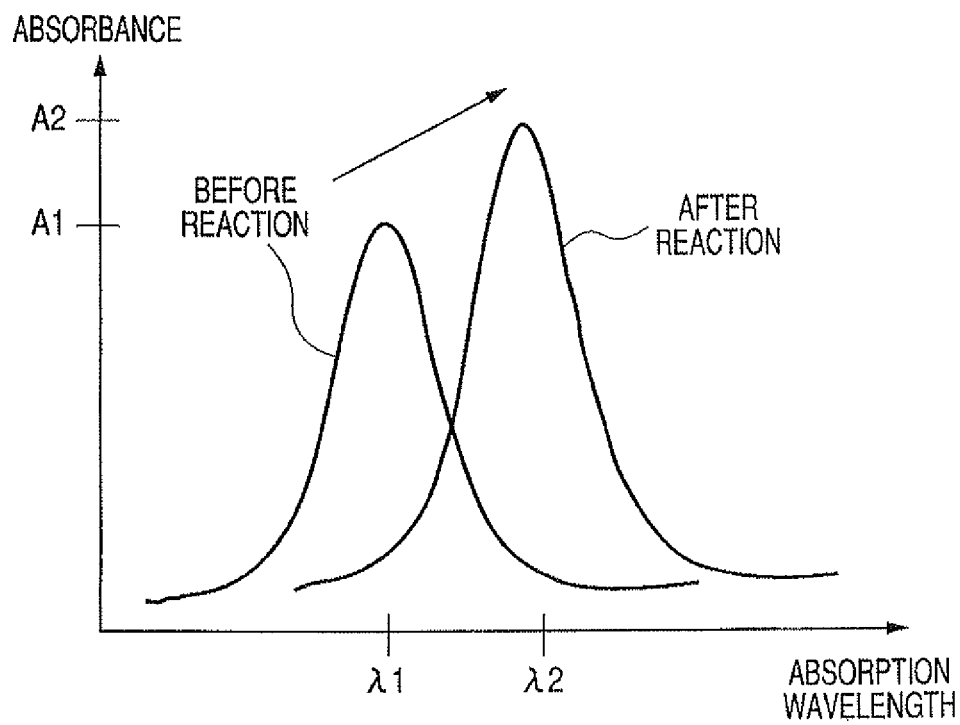
FIG. 15 is a graph illustrating the change in the detection spectrum (absorption spectrum) obtained in Example 2.

When the absorption spectrum is observed before and after the reaction, it will be found that a shift occurs to the absorption spectrum as shown in FIG. 15 as an example as the target substance is bound to the surface of the detection element due to a specific antigen-antibody reaction. The correlation of the peak intensity of the absorption spectrum or the extent of shift of the peak wavelength and the AFP concentration is determined in advance by means of a known AFP control solution so that it is possible to detect the minute AFP concentration of the specimen whose AFP concentration has not been known.

EXAMPLE 3 AND COMPARATIVE EXAMPLE 1

Figure 16:
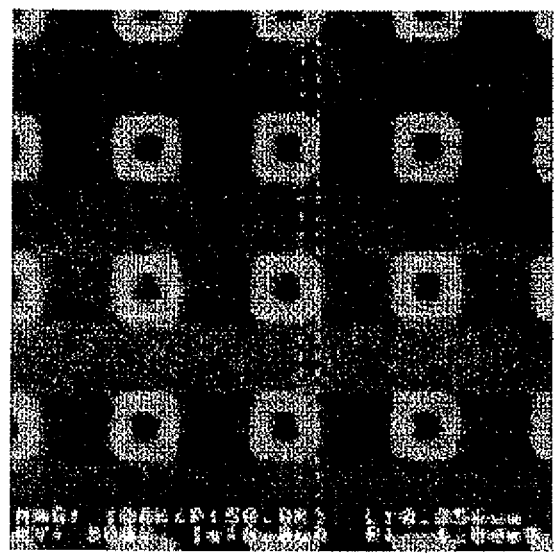
FIG. 16 is a schematic illustration of an SEM image obtained by detection element of Example 3.
Figure 17:
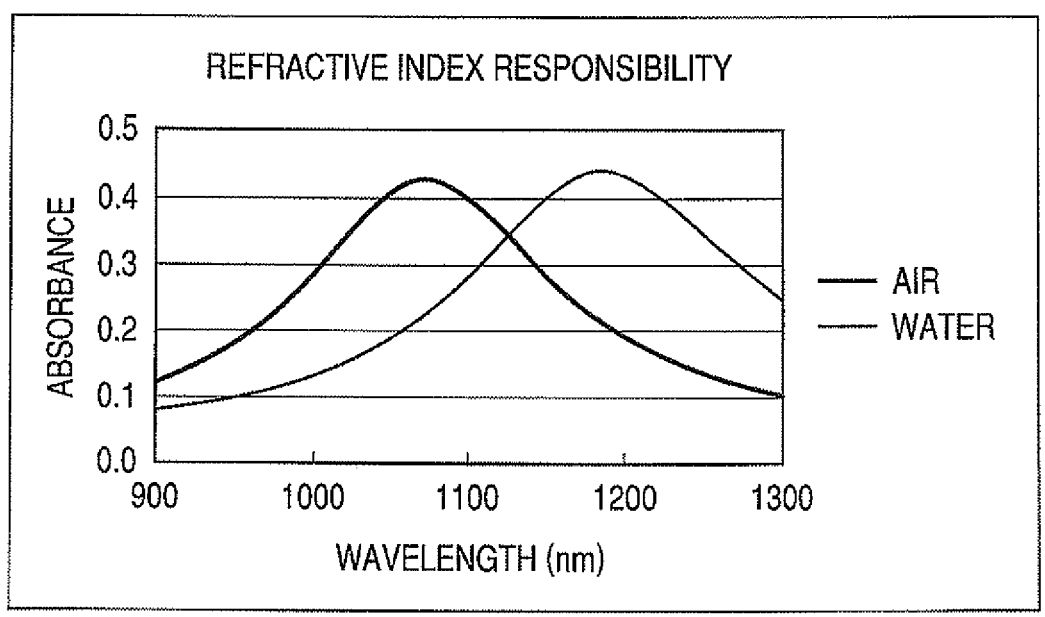
FIG. 17 is a graph illustrating the absorption spectrum obtained by the detection element of Example 3.

A detection apparatus similar to the one used in Example 1 was also used in this example except the configuration of the element is altered. The detection element of this example was prepared by forming a 20 nm-thick gold thin film on a 625 μm-thick quartz plate and patterning it to show a predetermined pattern by means of an electron beam lithography system. FIG. 16 is an image of the detection element obtained by means of a scanning electron microscope (SEM). As shown, the plane outer profile of each metal structure is ring-shaped with dimensions of 200 nm×200 nm and the belt width of each ring is 50 nm. It is not necessarily always possible to prepare the inside aperture so as to show a profile same as the outer profile of the metal structure because of the level of resolution. The structures are spaced apart by a distance of 250 nm and arranged in array in a region of 3 mm×3 mm. The absorption spectrum of the structures of this example shows a peak wavelength at or near 1,070 nm in the atmosphere. FIG. 17 shows the responsiveness relative to the refractive index as basic performance. The extent of shift of the peak wavelength relative to the refractive index is raised to about 1.4 times if compared with a pattern that is solid but has the same outer profile and same dimensions (Comparative Example 1) and hence does not have any ring-shaped circular structure.

Now, the method of fixing anti-AFP (α-fetoprotein) antibody, which is the target substance capturing body of this example, to the surface of the gold structure in order to provide the surface of the structure with a capturing ability will be described below. An ethanol solution of 11-mercaptoundecanoic acid that has a thiol group showing a strong affinity for gold, the material of the structure of this embodiment, is dropped on the element by means of a spotter to modify the surface of the structure. As a result, the carboxyl group is exposed on the surface of the structure. Under this condition, an aqueous solution of N-hydroxysulfosuccinimide (available from DOJINDO) and also an aqueous solution of 1-ethyl-3-[3-(dimethylamino)propyl]carbodiimide hydrochloride (available from DOJINDO) are dropped into the reaction region also by means of a spotter. As a result, the succinimide group is exposed on the surface of the structure. Then, the surface of the structure is modified as streptavidin is bound to it. Thereafter, biotinated anti-AFP antibody is fixed to the structure.

It is also possible to prepare a plurality of pattern regions for so many detection elements and different antibodies are respectively fixed to them so as to detect the different target substances contained in a specimen on the same substrate. Such an arrangement can be realized by using different antibodies and conducting a fixing operation similar to the above-described one.

The AFP concentration in the specimen can be specifically gauged by following an operation procedure similar to that of Example 1.

When the absorption spectrum is observed before and after the reaction, it will be found that a shift occurs to the absorption spectrum similar to that of Example 1 as the target substance is bound to the surface of the detection element due to a specific antigen-antibody reaction. The correlation of the peak intensity of the absorption spectrum or the extent of shift of the peak wavelength and the AFP concentration is determined in advance by means of a known AFP control solution so that it is possible to detect the minute AFP concentration of the specimen whose AFP concentration has not been known.

EXAMPLE 4

Figure 23:
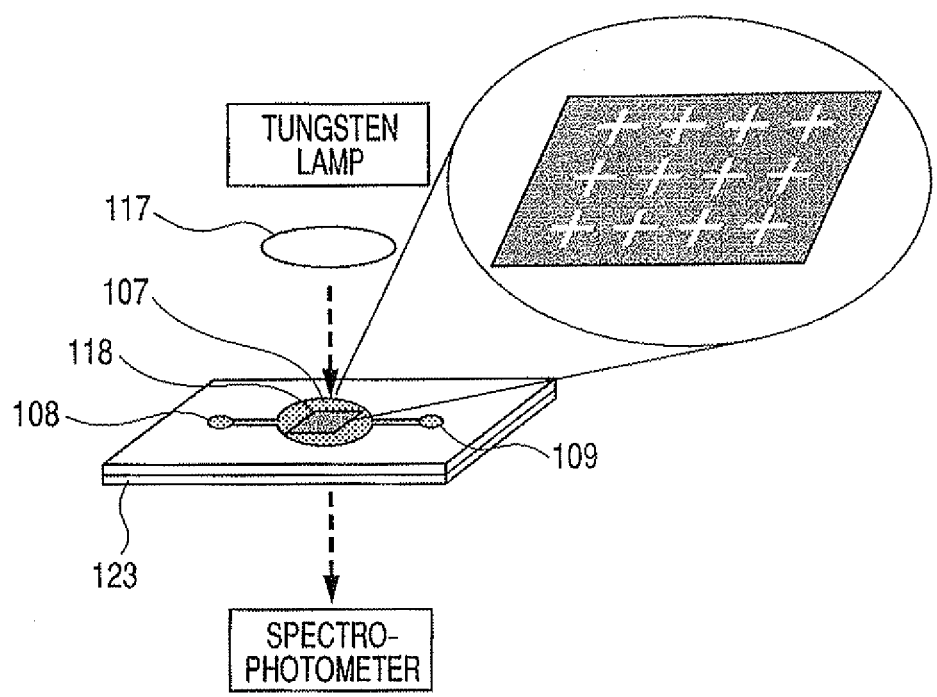
FIG. 23 is a schematic perspective view of the detection apparatus used in Example 4.

FIG. 23 schematically illustrates the structure of the detection apparatus used in this example. The detection element 118 was prepared by forming a 20 nm-thick gold thin film on a 625 μm-thick quartz plate and patterning it to show a predetermined pattern by means of an electron beam lithography system. The plane outer profile of the apertures was cross-shaped with dimensions of 200 nm×200 nm and the belt width was 50 nm. The apertures are spaced apart by a distance of 400 nm and arranged in array in a region of 3 mm×3 mm. In FIG. 23, the components denoted by respective reference symbols are same as those of the other comparable drawings denoted respectively by the same reference symbols and hence will not be described here any further.

Now, the method of fixing anti-AFP (α-fetoprotein) antibody, which is the target substance capturing body of this example, to the surface of the gold film in order to provide the surface of the gold film with a capturing ability will be described below. An ethanol solution of 11-mercaptoundecanoic acid that has a thiol group showing a strong affinity for gold, the material of the structure of this embodiment, is dropped on the element by means of a spotter to modify the film surface of the structure. As a result, the carboxyl group is exposed on the surface of the film. Under this condition, an aqueous solution of N-hydroxysulfosuccinimide (available from DOJINDO) and also an aqueous solution of 1-ethyl-3-[3-(dimethylamino)propyl]carbodimide hydrochloride (available from DOJINDO) are dropped into the reaction region also by means of a spotter. As a result, the succinimide group is exposed on the surface of the structure. Then, the surface of the structure is modified as streptavidin is bound to it. Thereafter, biotinated anti-AFP antibody is fixed to the structure.

It is also possible to prepare a plurality of pattern regions for so many detection elements and different antibodies are respectively fixed to them so as to detect the different target substances contained in a specimen on the same substrate. Such an arrangement can be realized by using different antibodies and conducting a fixing operation similar to the above-described one.

The AFP concentration in the specimen can be specifically gauged by following the operation procedure shown below. This will be described by referring to FIG. 10. The light source unit 112 and the spectrophotometer 113 are operated by inputting instructions by the input unit 119 and the program stored in the HDD 120 is loaded in the RAM 131 and executed. The obtained results are displayed on the display unit 115.

(1) The inlet 108 and the outlet 109 are connected respectively to the liquid feed pump 110 and the waste reservoir 116 and the detection chip 142 is arranged in such a way that the reaction well is disposed between the light source unit 112 and the spectrophotometer 113.

(2) The specimen that contains the target substance of AFP is introduced from the inlet 108 to have the AFP captured on the element 118 in the reaction well.

(3) The specimen is discharged from the outlet 109 and a phosphate buffer solution is introduced by way of the inlet 108 to clean the inside of the reaction well 107. The discharged solution is pooled in the waste reservoir 116.

(4) As the last step, the inside of the reaction well is filled with a phosphate buffer solution and light of a tungsten lamp is transmitted from the light source 112 to the element 118 in the reaction well to observe the absorption spectrum by means of the spectrophotometer 113.

When the absorption spectrum is observed before and after the reaction, a result similar to the one illustrated in FIG. 15 is obtained. In other words, it will be found that a shift occurs to the absorption spectrum as the target substance is bound to the surface of the detection element due to a specific antigen-antibody reaction. The correlation of the peak intensity of the absorption spectrum or the extent of shift of the peak wavelength and the AFP concentration is determined in advance by means of a known AFP control solution so that it is possible to detect the minute AFP concentration of the specimen whose AFP concentration has not been known.

EXAMPLE 5

Figure 31:
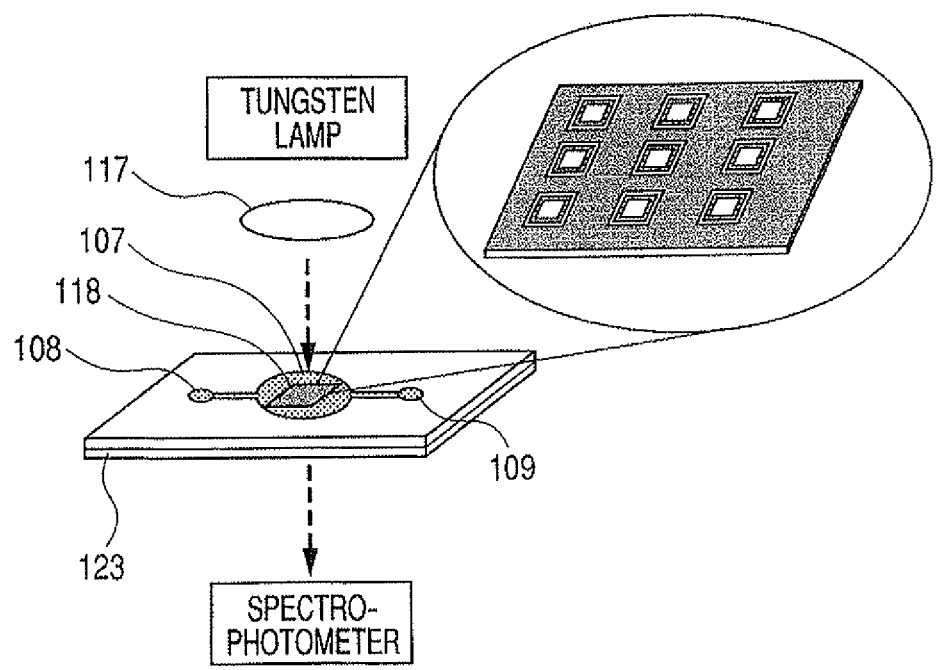
FIG. 31 is a schematic perspective view of the detection apparatus used in Example 1.

FIGS. 30 and 31 schematically illustrate the structure of the detection apparatus used in this example. The detection element 118 was prepared by forming a 20 nm-thick gold thin film 102 on a 625 μm-thick quartz plate 100 and patterning it to show a predetermined pattern by means of an electron beam lithography system. In the pattern, each complex structure 126 includes a small metal structure having an aperture of 400 nm and a minute metal structure of a 100 nm square arranged at the center of the aperture of the small metal structure. It is not necessarily always possible to prepare the inside aperture to show a profile similar to that of the outer profile of the small metal structure because of the level of resolution. The structures are spaced apart by a distance of 400 nm and arranged in array in a region of 3 mm×3 mm. The apparatus illustrated in FIG. 31 is obtained by altering only the detection element 118 of the apparatus illustrated in FIGS. 11 and 14 and described above. The components denoted by respective reference symbols are same as those of the comparable drawings denoted respectively by the same reference symbols and hence will not be described here any further.

Now, the method of fixing anti-AFP (α-fetoprotein) antibody, which is the target substance capturing body of this example, to the surface of the gold film in order to provide the surface of the complex metal structure with a capturing ability will be described below. An ethanol solution of 11-mercaptoundecanoic acid that has a thiol group showing a strong affinity for gold, the material of the structure of this embodiment, is dropped on the element by means of a spotter to modify the film surface of the structure. As a result, the carboxyl group is exposed on the surface of the film. Under this condition, an aqueous solution of N-hydroxysulfosuccinimide (available from DOJINDO) and also an aqueous solution of 1-ethyl-3-[3-(dimethylamino)propyl]carbodiimide hydrochloride (available from DOJINDO) are dropped into the reaction region also by means of a spotter. As a result, the succinimide group is exposed on the surface of the structure. Then, the surface of the structure is modified as streptavidin is bound to it. Thereafter, biotinated anti-AFP antibody is fixed to the structure.

It is also possible to prepare a plurality of pattern regions for so many detection elements and different antibodies are respectively fixed to them so as to detect the different target substances contained in a specimen on the same substrate. Such an arrangement can be realized by using different antibodies and conducting a fixing operation similar to the above-described one.

The AFP concentration in the specimen can be specifically gauged by following an operation procedure similar to that of Example 4.

When the absorption spectrum is observed before and after the reaction, a result similar to the one illustrated in FIG. 15 is obtained. In other words, it will be found that a shift occurs to the absorption spectrum as the target substance is bound to the surface of the detection element due to a specific antigen-antibody reaction. The correlation of the peak intensity of the absorption spectrum or the extent of shift of the peak wavelength and the AFP concentration is determined in advance by means of a known AFP control solution so that it is possible to detect the minute AFP concentration of the specimen whose AFP concentration has not been known.

EXAMPLE 6

In this example, a double-specific (diabody) that specifically shows affinity for two substances including gold that is the material of the detection element and HEL (hen egg white lysozyme) is used in order to provide the surface of the metal structure of the element of Example 1 with a capturing ability. The diabody as used herein is identical with the one described in Japanese Patent Application Laid-Open No. 2005-312446. The prepared diabody is added to the detection element section along with a phosphate buffer solution and, after an incubation process conduced for about 30 minutes, washed with the buffer solution. The technique of using a diabody of this example provides an advantage that it can be fixed without damaging the affinity if compared with a chemical fixation technique so that the quantity of the capturing body necessary for being fixed onto the detection element is reduced as a result.

The HEL concentration in the specimen can be specifically gauged by following the operation procedure shown below.
(1) The specimen containing the target substance of HEL is introduced into the prepared element by way of the inlet 108 to have the HEL captured on the structure (FIG. 11).
(2) The specimen is discharged and a phosphate buffer solution is introduced by way of the inlet 108 to clean the inside of the reaction well 107.
(3) As the last step, the inside of the reaction well is filled with a phosphate buffer solution to observe the absorption spectrum of the gold structure.

When the absorption spectrum is observed before and after the reaction, it will be found that a shift occurs to the absorption spectrum as shown in FIG. 13 as an example as the target substance is bound to the surface of the detection element due to a specific antigen-antibody reaction. The correlation of the peak intensity of the absorption spectrum or the extent of shift of the peak wavelength and the HEL concentration is determined in advance by means of a known HEL control solution so that it is possible to detect the minute HEL concentration of the specimen whose HEL concentration has not been known.

This application claims priorities from Japanese Patent Applications No. 2005-132929 filed Apr. 28, 2005 and No. 2005-370756 filed Dec. 22, 2005, which are hereby incorporated by reference herein.

The invention claimed is:

1. A substrate of a target substance detection element to be used for a detection apparatus for detecting a target substance, utilizing surface plasmon resonance, comprising:
a base; and
a plurality of metal members to give rise to localized surface plasmon resonance, arranged in an array as spaced apart from each other with a regular gap therebetween on a surface of the base, each of the metal members having at least either of a loop section and a crossing section.

2. The substrate according to claim 1, wherein each of the metal members has a largest length between two edges that is found within a range not smaller than 10 nm and not greater than 1,450 nm.

3. The substrate according to claim 2, wherein the largest length between two edges is found within a range not smaller than 50 nm and not greater than 450 nm.

4. The substrate according to claim 1, wherein any two adjacently located metal members are separated by a distance that is found within a range not smaller than 50 nm and not greater than 2,000 nm.

5. The substrate according to claim 4, wherein the distance separating any two adjacently located metal members is found within a range not smaller than 150 nm and not greater than 1,000 nm.

6. The substrate according to claim 1, wherein each of the metal members comprises an outer frame structure having an aperture and an inner structure arranged in the aperture and spatially separated from the outer frame structure.

7. A target substance detection element comprising:
a substrate according to any one of claims 1 to 6; and
a target substance capturing body arranged on each of the metal members.

8. An apparatus for detecting a target substance in a specimen by utilizing surface plasmon resonance, comprising:
holding means for holding a target substance detection element according to claim 7;
means for bringing the element into contact with the specimen; and
detecting means for detecting the target substance captured by the element.

9. The substrate according to claim 1, wherein the substrate further comprises a capturing body on the metals members for capturing the target substance.

10. A substrate of a target substance detection element to be used for a detection apparatus for detecting a target substance, utilizing surface plasmon resonance, comprising:
a base;
a metal film to give rise to surface plasmon resonance having a plurality of apertures, arranged in an array as spaced apart from each other with a regular gap therebetween on a surface of the base, each of the apertures having at least either of a loop section and a crossing section; and
a capturing body on the metal film for capturing the target substance.

11. The substrate according to claim 10, wherein any two adjacently located apertures are separated by a distance that is found within a range not smaller than 50 nm and not greater than 2,000 nm.

12. The substrate according to claim 11, wherein the distance separating any two adjacently located apertures is found within a range not smaller than 150 nm and not greater than 1,000 nm.

13. A target substance detection element comprising:
a substrate according to any one of claims 10 to 12; and
a target substance capturing body arranged on the metal film.

14. An apparatus for detecting a target substance in a specimen by utilizing surface plasmon resonance, comprising:
holding means for holding a target substance detection element according to claim 13;
means for bringing the element into contact with the specimen; and
detecting means for detecting the target substance captured by the element.

* * * * *